(12) United States Patent
Adams et al.

(10) Patent No.: US 6,464,638 B1
(45) Date of Patent: Oct. 15, 2002

(54) ULTRASOUND IMAGING SYSTEM AND METHOD FOR SPATIAL COMPOUNDING

(75) Inventors: Darwin P Adams, Lexington; Karl E Thiele, Andover, both of MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 55 days.

(21) Appl. No.: 09/680,382

(22) Filed: Oct. 5, 2000

(51) Int. Cl.$^7$ .................................................. A61B 8/00
(52) U.S. Cl. ...................................... 600/443; 600/447
(58) Field of Search ........................ 600/437, 443–447, 600/454–456; 73/625–630; 310/7, 11, 130, 320; 348/224; 382/128

(56) References Cited

U.S. PATENT DOCUMENTS

| | | | |
|---|---|---|---|
| 4,350,917 A | 9/1982 | Lizzi et al. .................. | 310/320 |
| 4,431,007 A | 2/1984 | Amazeen et al. ........... | 128/660 |
| 5,129,399 A | 7/1992 | Hirama ........................ | 128/661 |
| 5,322,068 A | 6/1994 | Thiele et al. ............... | 128/661 |
| 5,409,007 A | 4/1995 | Saunders et al. ........... | 128/661 |
| 5,421,333 A | 6/1995 | Takamizawa et al. ....... | 128/661 |
| 5,479,926 A * | 1/1996 | Ustuner et al. ............. | 348/224 |
| 5,546,946 A | 8/1996 | Souquet ...................... | 128/662 |
| 5,566,674 A | 10/1996 | Weng ........................... | 128/660 |
| 5,653,235 A | 8/1997 | Teo ............................. | 128/661 |
| 5,734,738 A | 3/1998 | Sato ............................ | 382/128 |
| 5,908,390 A | 6/1999 | Matsushima ................ | 600/447 |
| 5,957,852 A | 9/1999 | Hossack et al. ............. | 600/477 |
| 6,057,632 A | 5/2000 | Ustuner ....................... | 310/334 |
| 6,117,081 A | 9/2000 | Jago et al. .................. | 600/443 |
| 6,193,663 B1 * | 2/2001 | Napolitano et al. ......... | 600/447 |
| 6,224,552 B1 * | 5/2001 | Jago et al. .................. | 600/437 |

OTHER PUBLICATIONS

Web Page, http://www.classicmedical.com/review.to.html, Transducers and Oxymorons, by Raymond L. Pow is, Ph.D., Dated: Aug. 4, 2000, pp. 1–2.

* cited by examiner

Primary Examiner—Marvin M. Lateef
Assistant Examiner—Ali M. Imam
(74) Attorney, Agent, or Firm—John Vodopia

(57) ABSTRACT

An ultrasound imaging system is provided along with a method for spatially compounding a plurality of ultrasound images in an elevation dimension. The ultrasound imaging system and method reduce image speckle. The ultrasound imaging system may include a transducer in electrical communication with an ultrasound system controller configured to generate, transmit, and receive a series of ultrasound energy pulses. The ultrasound system controller is further configured to recover image information using beamforming techniques from steered or focused ultrasound imaging planes prior to spatial compounding of a plurality of image frames. The present invention may also be broadly viewed as providing a method for ultrasound imaging. Briefly stated, the method comprises the following steps: generating a transmit scan beam; generating a plurality of ultrasound response scan beams originating from spatially separated vantage points such that corresponding response scan beams converge at the transmit scan beam; deriving image information from the plurality of ultrasound response scan beams; and compounding the image information in the elevation direction.

32 Claims, 11 Drawing Sheets

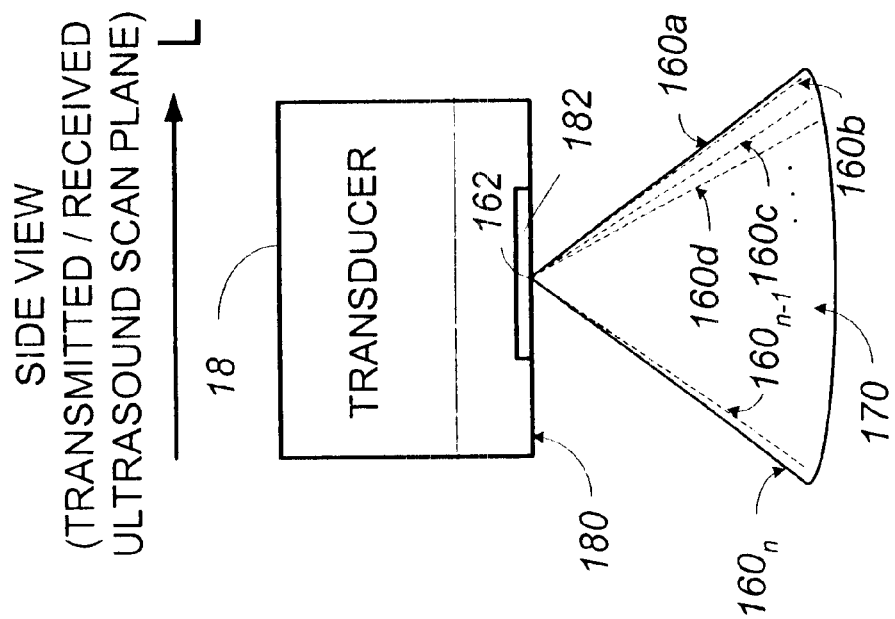
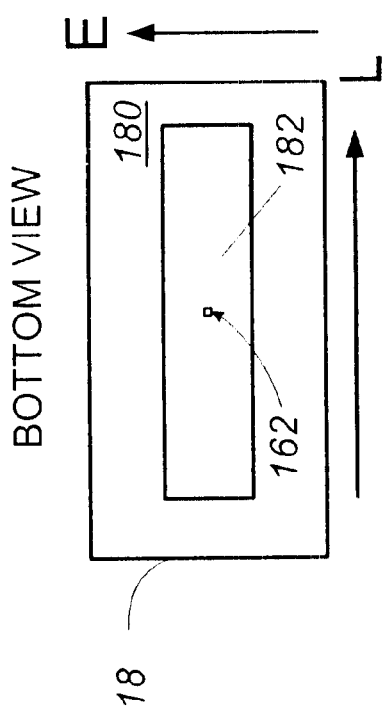
FIG. 4

FIG. 8
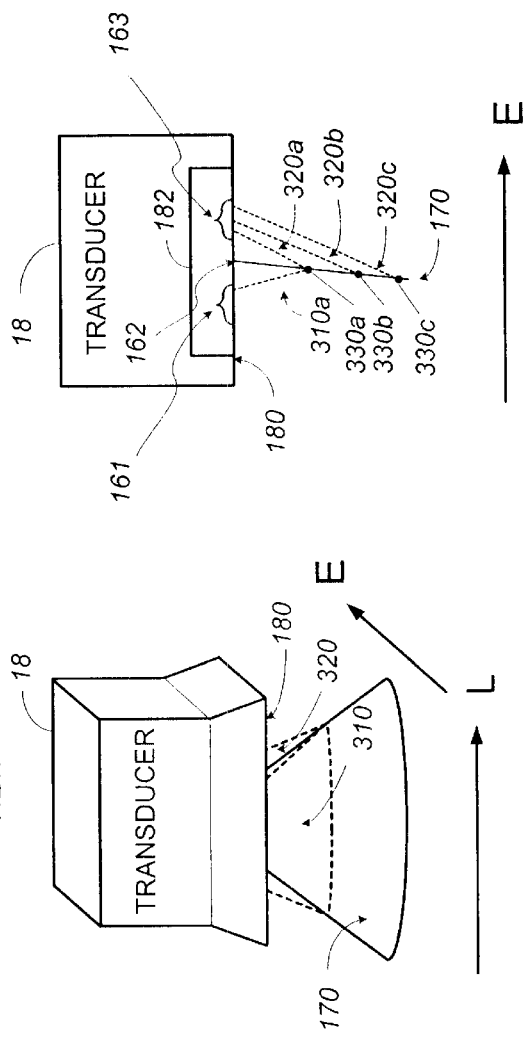
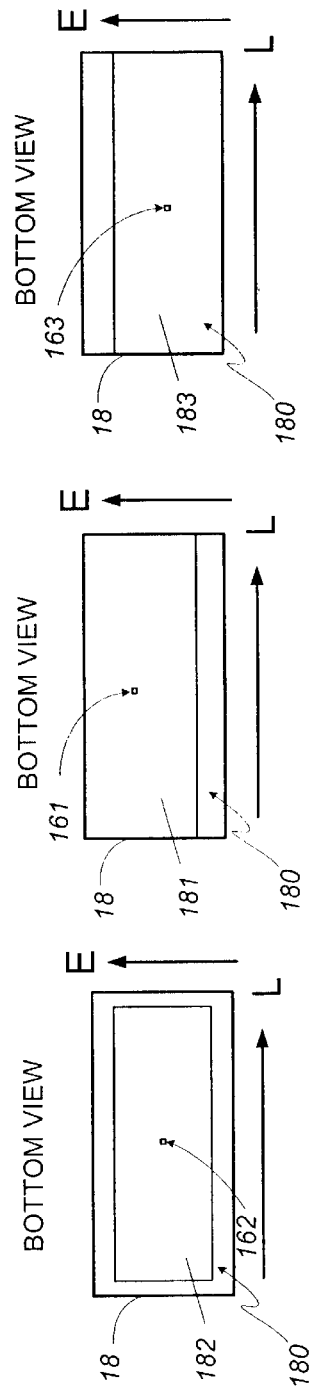

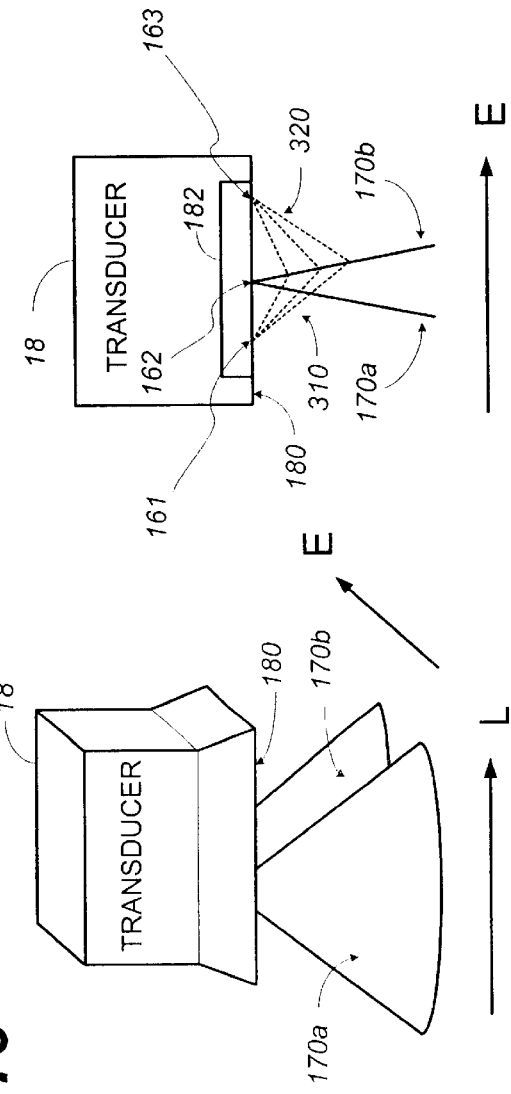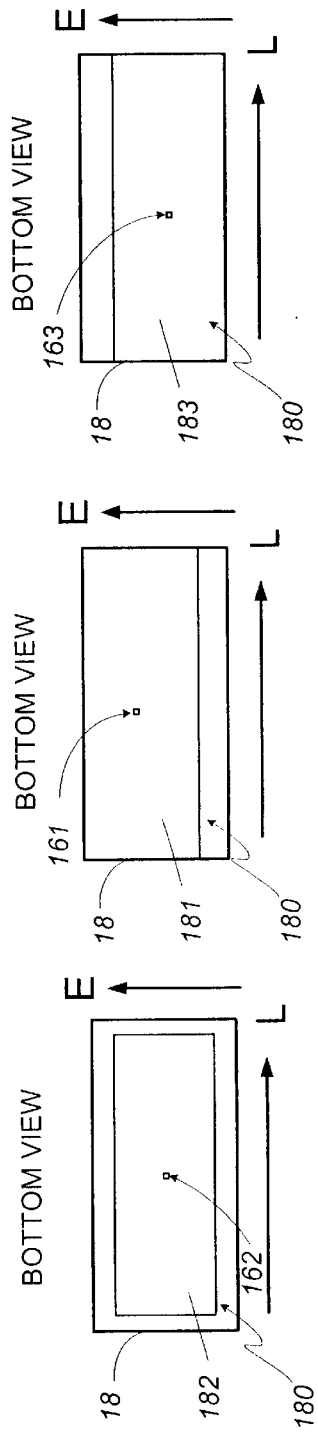
FIG. 10

ULTRASOUND IMAGING SYSTEM AND METHOD FOR SPATIAL COMPOUNDING

FIELD OF THE INVENTION

The present invention is generally related to ultrasound imaging systems, and more particularly, to an ultrasound imaging system and method that employs spatial compounding to reduce speckle in ultrasound imaging.

BACKGROUND OF THE INVENTION

Ultrasonic imaging has become an important and popular diagnostic tool with a wide range of applications. Particularly, due to its non-invasive and typically non-destructive nature, ultrasound imaging has been used extensively in the medical profession. Modem high-performance ultrasound imaging systems and techniques are commonly used to produce two-dimensional diagnostic images of internal features of an object (e.g., portions of the anatomy of a human patient). A diagnostic ultrasound imaging system generally uses a wide bandwidth transducer to emit and receive ultrasound signals. The ultrasound imaging system forms images of the internal tissues of a human body by electrically exciting an acoustic transducer element or an array of acoustic transducer elements to generate ultrasonic pulses that travel into the body. The ultrasonic pulses produce echoes as they reflect off of body tissues that appear as discontinuities to the propagating ultrasonic pulses. The various echoes return to the transducer and are converted into electrical signals that are amplified and processed to produce an image of the tissues. These ultrasonic imaging systems are of significant importance to the medical field by providing physicians real-time high-resolution images of internal features of a human anatomy without resort to more invasive exploratory observation techniques such as surgery.

Ultrasonic imaging systems employ an acoustic transducer to radiate and receive a plurality of ultrasonic pulses. The acoustic transducer, which radiates the ultrasonic pulses, typically comprises a piezoelectric element or an array of piezoelectric elements. As is known in the art, a piezoelectric element deforms upon application of an electrical signal to produce the transmitted ultrasonic pulses. Similarly, the received echoes cause the piezoelectric element to deform and generate a corresponding receive electrical signal. The acoustic transducer is often packaged in a handheld device that allows an operator substantial freedom to manipulate the transducer over a desired area of interest. The transducer is often connected via a cable to a control device that generates and processes the electrical signals. In turn, the control device may transmit image information to a real-time viewing device, such as a display monitor. In alternative configurations, the image information may also be transmitted to physicians at a remote location and or stored in a recording device to permit viewing of the diagnostic images at a later time.

One fundamental problem in all types of ultrasound imaging is noise from back-scattered signals, which obscures the details of the target image or echo. One type of noise, commonly known as "speckle," results from constructive and destructive interference, and appears as a random mottle superimposed on the image. Normally, speckle is received from objects having dimensions smaller than the wavelengths generated by the ultrasound energy source, making it impossible to reduce the speckle simply by increasing the resolution of the device. Moreover, speckle originates from objects that are stationary and randomly distributed. Since the speckle has no phase or amplitude variation over time, one cannot suppress the speckle by averaging the image signals over time. In other words, speckle signals are coherent and cannot be reduced by time averaging.

One way to reduce speckle is through a method known as spatial compounding. The idea is to insonify a target image with ultrasonic energy and receive or capture the target image from a number of different vantage points. The multiple received images related to each of the various vantage points are then mathematically combined to reduce the speckle. The success of the method is due to the statistical independence of the speckle patterns when viewed from multiple vantage points, and the fact that the target size is much larger than the speckle causing scatterers. By mathematically combining (e.g., averaging) a plurality of images formed from information gathered from a number of vantage points, the speckle patterns lack correlation, while the target echoes remain correlated and virtually unchanged. As a result of the lack of correlation in the speckle patterns between the various vantage points, the variance in the speckle patterns can be reduced without degrading the target image. The calculations to mathematically combine images formed from different vantage points for reducing speckle are well known.

There are two known methods for generating a spatially compounded ultrasound image. A first method, uses a conventional transducer that is moved to various vantage points with an articulated arm to acquire the necessary images. The transducer location is accurately measured by sensing devices in order to locate each of the images. An example of a compound image scanner using angular sensing devices on an arm assembly is disclosed in U.S. Pat. No. 4,431,007, to Amazeen et al., entitled, "Referenced Real-Time Ultrasonic Image Display." In practice, however, the arm assembly is awkward and inflexible to operate, and the sensing devices add significant complexity and cost to the ultrasonic imaging system. A second technique uses a transducer having an array of transducer elements to generate two or more images at slightly different viewing angles from a fixed transducer location.

Typically, the way to generate multiple images from different directions with a "fixed" transducer is to excite different cells or groups of cells of a linear or curved linear array of piezoelectric transducer elements, which are used to generate and receive the ultrasound energy. The vantage point for an ultrasound beam is typically controlled by the physical position of an active aperture used for forming the ultrasound beam. Thus the groups in a fixed transducer must be separated along the array in order to achieve the required spatially separated vantage points.

By way of example, one can separate a linear array of N transducer elements into M sections, each section having N/M contiguous transducer elements and defined by an unique location or vantage point along the array. Each section may be electrically excited one at a time in succession with the resulting ultrasound beam from each of the transducer sections steered so that all M beams are focused at substantially the same region, but from different directions having their origin at the face of the transducer array. Speckle can then be reduced by combining the M ultrasound beams (controlled by both transmit and receive processing) from the related M different vantage points. A problem with such methods is that in order to control the location of the vantage points, the transmit and receive apertures must be reduced since the aperture locations in part define the origin of the ultrasound beams and hence the vantage point. Instead of using the entire transducer element array, the transducer element section method described above uses portions of the transducer element array, which may significantly reduce the aperture size of the transducer array and the lateral resolution of the reflected images. In addition, the reduced aperture size of such methods may significantly reduce the signal strength and decreases the signal to noise ratio for the received target echoes.

Another known method for compounding an ultrasonic image is to perform a technique known as frequency compounding. An example of a frequency compounding technique is disclosed in U.S. Pat. No. 4,350,917, to Lizzi et al., entitled, "Frequency-Controlled Scanning of Ultrasonic Beams." In accordance with Lizzi, a transducer having a piezoelectric element may be used with a transmit signal having a varying frequency to control the radiation direction of an ultrasound transmit beam. A problem with frequency compounding is that the axial resolution may be adversely affected.

The design of a system using spatial compounding usually involves engineering trade-offs and compromises. In a real time system, frame rates may be reduced because two or more images must be used to form each frame. In addition, larger apertures or several apertures must be used to provide different vantage points from which to create images. If the images are not created simultaneously, they must be buffered prior to being combined. As a result, additional resources, such as transducer apertures, related processing channels, and image buffer memory, can increase system cost and increase the size of both transducers and the ultrasound imaging systems.

All prior art techniques used to reduce ultrasound image speckle have the undesired consequence of reducing lateral and/or axial resolution of the target image. For example, lateral spatial compounding reduces lateral resolution of the image. By way of further example, frequency compounding reduces axial resolution of the image.

As a result, there is a need for a system and method that provides an improved two-dimensional image with reduced image speckle.

SUMMARY OF THE INVENTION

The present invention provides for an ultrasound imaging system configured to transmit and receive a plurality of ultrasound planes spatially separated and/or steered in elevation, to spatially compound in the elevation dimension for the purpose of creating an improved two-dimensional ultrasound image having reduced speckle.

Architecturally, the ultrasound imaging system may include a phased, linear, or curved linear array transducer in electrical communication with an ultrasound system controller configured to generate and forward a series of excitation signals to the transducer. The ultrasound imaging system may work in conjunction with the transducer to transmit ultrasound energy into a region of interest in a patient's body along a plurality of transmit lines. A transmit scan beam may be defined by a plurality of transmit scan lines. The ultrasound imaging system, may further comprise a receiver for receiving ultrasound echoes with the transducer from the region of interest in response to the ultrasound energy and for generating received signals representative of the received ultrasound echoes. The system may also comprise a parallel beamformer for processing a plurality of received signals to form first and second sets of received ultrasonic beams which originate at first and second spatially separated vantage points, respectively. In accordance with the present invention, a plurality of received ultrasonic scan beams may be steered and focused at multiple points along the transmit scan beam to simultaneously generate first and second beamformer signals representative of ultrasound echoes received along each of the transmit lines.

The ultrasound imaging system is further configured to receive and recover information from ultrasound target echoes for further processing by any number of devices capable of translating the recovered ultrasound target echo information into a viewable image.

The present invention may also be broadly viewed as providing a method for ultrasound imaging. Briefly stated, the method comprises the following steps: transmitting ultrasound energy into a region of interest such that a transmit scan beam is formed; recovering a plurality of steered ultrasound response planes from ultrasonic echoes, each ultrasound response plane having a separately defined vantage point such that at least two ultrasound response planes are focused or steered in the elevation dimension to intersect at the transmit scan beam; deriving image information from the plurality of ultrasound response planes; and compounding the image information in the elevation direction.

In accordance with the method for ultrasound imaging, a plurality of response planes are steered and focused such that corresponding response planes intersect the transmit beam at a plurality of predetermined points along each of the transmit scan beams to simultaneously generate first and second beamformed signals representative of ultrasound echoes received at various distances from the transducer face along each of the transmit scan beams. The first and second beamformed signals are detected to form first and second detected signals, respectively. In the preferred embodiment of an ultrasound imaging system of the present invention, the first and second detected signals are mathematically combined to provide an image producing signal representative of an image of the region of interest.

In accordance with a first preferred embodiment of the method for ultrasound imaging, the response planes are received through first and second apertures, respectively, of a transducer array. The first and second apertures may be varied dynamically during reception of ultrasound echoes along each of the transmit lines.

In accordance with a second preferred embodiment of the method for ultrasound imaging, the first and second spatial vantage points may be maintained in fixed positions by defining fixed first and second apertures during reception of ultrasound echoes for each of the transmit lines.

In accordance with an alternative embodiment of the method for ultrasound imaging, a plurality of substantially parallel transmit scan beams closely separated in the elevation dimension may be applied to a region of interest. A plurality of spatially separated vantage points defined by respective apertures on the transducer array may be used to recover a plurality of response planes steered and focused to intersect at each of the respective transmit scan beams.

In accordance with another alternative embodiment of the method for ultrasound imaging, one or more of the aforementioned methods for spatially compounding in the elevation dimension is combined with one or more prior art methods for spatial compounding.

Other features and advantages of the invention will become apparent to one skilled in the art upon examination of the following drawings and detailed description. These additional features and advantages are intended to be included herein within the scope of the present invention.

BRIEF DESCRIPTION OF THE DRAWINGS

FIG. 4 is a schematic diagram further illustrating the generation of an exemplary transmit scan beam that may be formed by the ultrasound imaging system of FIGS. 1 and 2;

FIG. 8 is a composite of a front perspective, side, and bottom views illustrating the orientation of the plurality of ultrasound image planes in a second embodiment of an ultrasound imaging system in of FIGS. 1 and 2;

FIG. 10 is a composite of a front perspective, side, and bottom views illustrating the orientation of the plurality of ultrasound image planes in a fourth embodiment of an ultrasound imaging system of FIGS. 1 and 2.

DETAILED DESCRIPTION OF THE INVENTION

Figure 1:
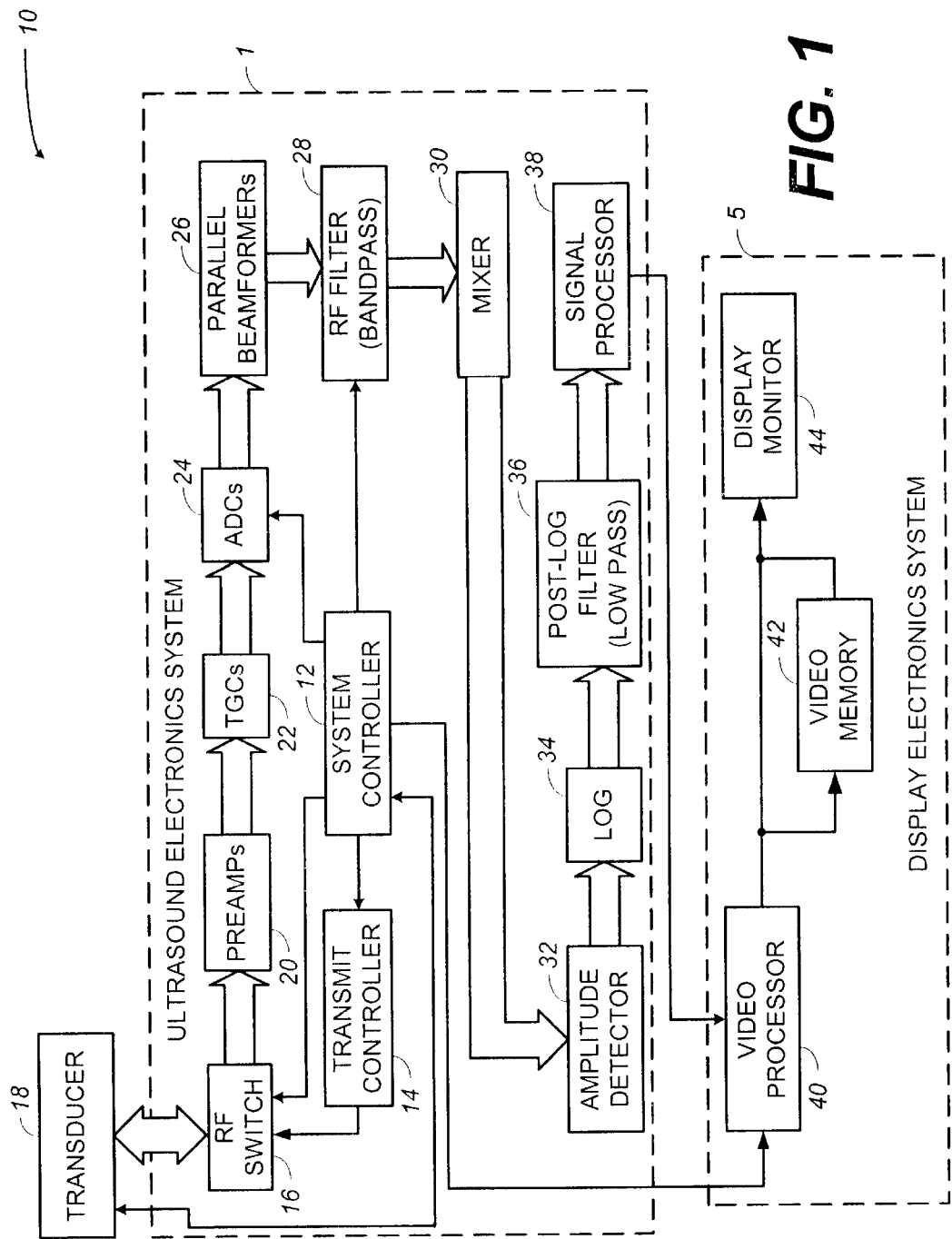
FIG. 1 is a block diagram of an ultrasound imaging system in accordance with the present invention that may practice the method of the present invention.

The improved ultrasound imaging system and method of the present invention will now be specifically described in detail in the context of an ultrasound imaging system that creates and displays brightness mode (B-Mode) images, or gray-scale images, which are well known in the art. However, it should be noted that the ultrasound imaging system and method of the present invention may be incorporated in other ultrasound imaging systems, including but not limited to, color flow imaging systems and other ultrasound imaging systems that are suited for the method, as will be apparent to those skilled in the art.

The present invention will be more fully understood from the detailed description given below and from the accompanying drawings of the preferred embodiment of the invention, which however, should not be taken to limit the invention to the specific embodiments enumerated, but are for explanation and for better understanding only. Furthermore, the drawings are not necessarily to scale, emphasis instead being placed upon clearly illustrating the principles of the invention. Finally, like reference numerals in the figures designate corresponding parts throughout the several drawings.

System Architecture and Operation

The architecture of an ultrasound imaging system capable of implementing the method of the present invention is illustrated by way of a functional block diagram in FIG. 1 and is generally denoted by reference numeral 10. Note that many of the functional blocks illustrated in FIG. 1 define a logical function that can be implemented in hardware, software, or a combination thereof. For purposes of achieving high speed, it is preferred, at present, that most of the blocks be implemented in hardware, unless specifically noted hereafter.

Referring to FIG. 1, the ultrasound imaging system 10 may include an ultrasound electronics system 1 in communication with a transducer 18 and display electronics system 5. As illustrated in FIG. 1, the ultrasound electronics system 1 may include a system controller 12 designed to control the operation and timing of the various elements and signal flow within the ultrasound imaging system 10 pursuant to suitable software. The ultrasound electronics system 1 may further comprise a transmit controller 14, a radio-frequency (RF) switch 16, a plurality of preamps 20, time-gain compensators (TGCs) 22, and analog to digital converters (ADCs) 24. In addition, the ultrasound electronics system 1 may comprise a parallel beamformer 26, a RF filter 28, a mixer 30, an amplitude detector 32, a log mechanism 34, a post-log filter 36, and a signal processor 38. As further illustrated in FIG. 1, the display electronics system 5 may comprise a video processor 40, a video memory device 42, and a display monitor 44.

The transducer 18 configured to emit and receive ultrasound signals, or acoustic energy, respectively to and from an object under test (e.g., the anatomy of a patient when the ultrasound imaging system 10 is used in the context of a medical application), is preferably a phased array transducer having a plurality of elements both in the lateral and elevation directions as will be further explained with regard to FIGS. 3A and 3B.

In the preferred embodiment, the transducer 18 comprises an array of elements typically made of a piezoelectric material, for example but not limited to, lead zirconate titanate (PZT). Each element is supplied with an electrical pulse or other suitable electrical waveform, causing the elements to collectively propagate an ultrasound pressure wave into the object under test. Moreover, in response thereto, one or more echoes are reflected by the object under test and are received by the transducer 18, which transforms the echoes into an electrical signal for further processing.

The array of elements associated with the transducer 18 enable a beam, emanating from the transducer array, to be steered (during transmit and receive modes) through the object by delaying the electrical pulses supplied to the separate elements. When the transmit mode is active, an analog waveform is communicated to each transducer element, thereby causing a pulse to be selectively propagated in a particular direction, like a beam, through the object.

When the receive mode is active, an analog waveform is received at each transducer element at each beam position. Each analog waveform essentially represents a succession of echoes received by the transducer element over a period of time as echoes are received along the single beam through the object. Time delays are applied to the signals from each element in order to form a narrow receive beam in the desired direction. The entire set of analog waveforms formed by both transmit and receive mode manipulations represents an acoustic line, and the entire set of acoustic lines represents a single view, or image, of an object and is referred to as a frame.

As is known, a phased-array transducer may comprise a host of internal electronics responsive to one or more control signals that may originate within the system controller 12 or alternatively in the transmit controller 14. For example, the transducer electronics may be configured to select a first subset of transducer elements to apply an excitation signal in order to generate a plurality of ultrasonic pulses. In a related manner, the transducer electronics may be configured to select a second subset of transducer elements to receive ultrasonic echoes related to the transmitted ultrasonic pulses. Each of the aforementioned transducer element selections may be made by the transducer 18 in response to the one or more control signals originating in the transmit controller 14 or the system controller 12.

As illustrated in FIG. 1, the transmit controller 14 may be electrically connected to the transducer 18 via a RF switch 16. The transmit controller 14 maybe in further communication with the system controller 12. The system controller 12 may be configured to send one or more control signals in order to direct operation of the transmit controller 14. In response, the transmit controller 14 may generate a series of electrical pulses that may be periodically communicated to a portion of the array of elements of the transducer 18 via the RF switch 16, causing the transducer elements to emit ultrasound signals into the object under test of the nature described previously. The transmit controller 14 typically provides separation between the pulsed transmissions to enable the transducer 18 to receive echoes from the object during the period therebetween and forwards them onto a set of parallel analog preamplifiers 20, herein labeled, "PREAMPs." The RF switch 16 may be configured to direct the various transmit and receive electrical signals to and from the transducer 18.

The plurality of preamplifiers 20 may receive a series of analog electrical echo waveforms from the transducer 18 that are generated by echoes reflected from the object under test. More specifically, each preamplifier 20 receives an analog electrical echo waveform from a corresponding set of transducer elements for each acoustic line. Moreover, the set of preamplifiers 20 receives a series of waveform sets, one set for each separate acoustic line, in succession over time and may process the waveforms in a pipeline processing manner. The set of preamplifiers 20 may be configured to amplify the echo waveforms to provide amplified echo waveforms in order to enable further signal processing, as described hereafter. Because the ultrasound signals received by the transducer 18 are of low power, the set of preamplifiers 20 should be of sufficient quality that excessive noise is not generated in the process.

Because the echo waveforms typically decay in amplitude as they are received from progressively deeper depths in the object under test, the plurality of analog preamplifiers 20 in the ultrasound electronics system 1 may be connected respectively to a parallel plurality of TGCs 22, which are known in the art and which are designed to progressively increase the gain during each acoustic line, thereby reducing the dynamic range requirements on subsequent processing stages. Moreover, the set of TGCs 22 may receive a series of waveform sets, one set for each separate acoustic line, in succession over time and may process the waveforms in a pipeline processing manner.

A plurality of parallel analog-to-digital converters (ADCs) 24 may be in communication respectively with the plurality of TGCs 21, as shown in FIG. 1. Each of the ADCs 22 may be configured to convert its respective analog echo waveform into a digital echo waveform comprising a number of discrete location points (hundreds to thousands; corresponding with depth and may be a function of ultrasound transmit frequency or time) with respective quantized instantaneous signal levels, as is well known in the art. In previous prior art ultrasound imaging systems, this conversion often occurred later in the signal processing steps, but now, many of the logical functions that are performed on the ultrasonic signals can be digital, and hence, the conversion is preferred at an early stage in the signal processing process. Similar to the TGCs 22, the plurality of ADCs 24 may receive a series of waveforms for separate acoustic lines in succession over time and process the data in a pipeline processing manner. As an example, the system may process signals at a clock rate of 40 MHz with a B-mode frame rate of 60 Hz.

A set of parallel beamformers 26 may be in communication with the plurality of ADCs 24 and may be designed to receive the multiple digital echo waveforms (corresponding with each set of transducer elements) from the ADCs 24 and combine them to form a single acoustic line. To accomplish this task, each parallel beamformer 26 may delay the separate echo waveforms by different amounts of time and then may add the delayed waveforms together, in order to create a composite digital RF acoustic line. The foregoing delay and sum beamforming process is well known in the art. Furthermore, the parallel beamformer 26 may receive a series of data collections for separate acoustic lines in succession over time and process the data in a pipeline processing manner.

A RF filter 28 may be coupled to the output of the parallel beamformers 26 and may be configured to receive and process a plurality of digital acoustic lines in succession. The RF filter 28 may be in the form of a bandpass filter configured to receive each digital acoustic line and to remove undesired out of band noise. As further illustrated in FIG. 1, a mixer 30 may be coupled at the output of the RF filter 28. The mixer 30 may be designed to process a plurality of digital acoustic lines in a pipeline manner. The mixer 30 may be configured to combine the filtered digital acoustic lines from the RF filter 28 with a local oscillator signal (not shown for simplicity) in order to ultimately produce a plurality of baseband digital acoustic lines. Preferably, the local oscillator signal is a complex signal, having an in-phase signal (real) and a quadrature phase signal (imaginary) that are ninety degrees out of phase. The result of the mixing operation may produce sum and difference frequency signals. The sum frequency signal may be filtered (removed), leaving the difference frequency signal, which is a complex signal at near zero frequency. A complex signal is desired in order to follow direction of movement of anatomical structures imaged in the object under test, and to allow accurate, wide bandwidth amplitude detection.

Up to this point in the ultrasound echo receive process, all operations can be considered substantially linear, so that the order of operations may be rearranged while maintaining substantially equivalent function. For example, in some systems it may be desirable to mix to a lower intermediate frequency (IF) or to baseband before beamforming or filtering. Such rearrangements of substantially linear processing functions are considered to be within the scope of this invention.

An amplitude detector 32 may receive and process, in pipeline manner, the complex baseband digital acoustic lines from the mixer 30. For each complex baseband digital acoustic line, the amplitude detector 32 may analyze the envelope of the line to determine the signal intensity at each point along the acoustic line to produce an amplitude-detected digital acoustic line. Mathematically, this means that the amplitude detector 32 determines the magnitude of each phasor (distance to origin) corresponding with each point along the acoustic line.

A log mechanism 34 may receive the amplitude-detected digital acoustic lines in a pipeline processing manner, from the amplitude detector 32. The log mechanism 34 may be configured to compress the dynamic range of the data by computing the mathematical logarithm (log) of each acoustic line to produce a compressed digital acoustic line for further processing. Implementation of a log function enables a more realistic view, ultimately on a display, of the change in brightness corresponding to the ratio of echo intensities.

A post-log filter 36, usually in the form of a low-pass filter, may be coupled to the output of the log mechanism 34 and may be configured to receive the compressed digital acoustic lines in a pipeline fashion. The post-log filter 36 may remove or suppress high frequencies associated with the compressed digital acoustic lines in order to enhance the quality of the ultimate display image. Generally, the post-log filter 36 softens the speckle in the displayed image. The low-pass post-log filter 36 can also be configured to perform anti-aliasing. The low-pass post-log filter 36 can be designed to essentially trade spatial resolution for gray-scale resolution.

A signal processor 38 may be coupled to the output of the low-pass post-log filter 36. The signal processor 38 may further comprise a suitable species of random access memory (RAM) and may be configured to receive the filtered digital acoustic lines from the low-pass post-log filter 36. The acoustic lines can be defined within a two-dimensional coordinate space. The signal processor 38 may be configured to mathematically manipulate image information within the received and filtered digital acoustic lines. In an alternative embodiment, the signal processor 38 may be configured to accumulate acoustic lines of data over time for signal manipulation. In this regard, the signal processor 38 may further comprise a scan converter to convert the data as stored in the RAM in order to produce pixels for display. The scan converter may process the data in the RAM once an entire data frame (i.e., a set of all acoustic lines in a single view, or image/picture to be displayed) has been accumulated by the RAM. For example, if the received data is stored in RAM using polar coordinates to define the relative location of the echo information, the scan converter may convert the polar coordinate data into rectangular (orthogonal) data capable of raster scan via a raster scan capable processor.

Having completed the receiving, echo recovery, and signal processing functions, to form a plurality of image frames associated with the plurality of ultrasound image planes, the ultrasound electronics system 1 may spatially compound the plurality of image frames in elevation by mathematically combining (e.g., averaging) the plurality of image frames to form a single image frame with reduced speckle. Having spatially compounded the plurality of image frames in the elevation direction, the ultrasound electronics system 1 may forward the echo image data information associated with the single spatially-compounded image frame to a display electronics system 5 as illustrated in FIG. 1. The display electronics system 5 may receive the echo image data from the ultrasound electronics system 1, where the echo image data may be forwarded to a video processor 40. The video processor 40 may be designed to receive the echo image data information and may be configured to raster scan the image information. The video processor 40 outputs picture elements (e.g., pixels) for storage in a video memory device 42 and/or for display via a display monitor 44. The video memory device 42 may take the form of a digital video disk (DVD) player/recorder, a compact disc (CD) player/recorder, a video cassette recorder (VCR) or other various video information storage devices. As is known in the art, the video memory device 42 permits viewing and or post data collection image processing by a user/operator in other than real-time.

A conventional display device in the form of a display monitor 44 may be in communication with both the video processor 40 and the video memory 42 as illustrated in FIG. 1. The display monitor 44 may be configured to periodically receive the pixel data from either the video memory 42 and or the video processor 40 and drive a suitable screen or other imaging device (e.g., a printer/plotter) for viewing of the ultrasound image by a user/operator.

Spatial Compounding in an Elevation Direction

Fundamental Image Formation

Figure 2:
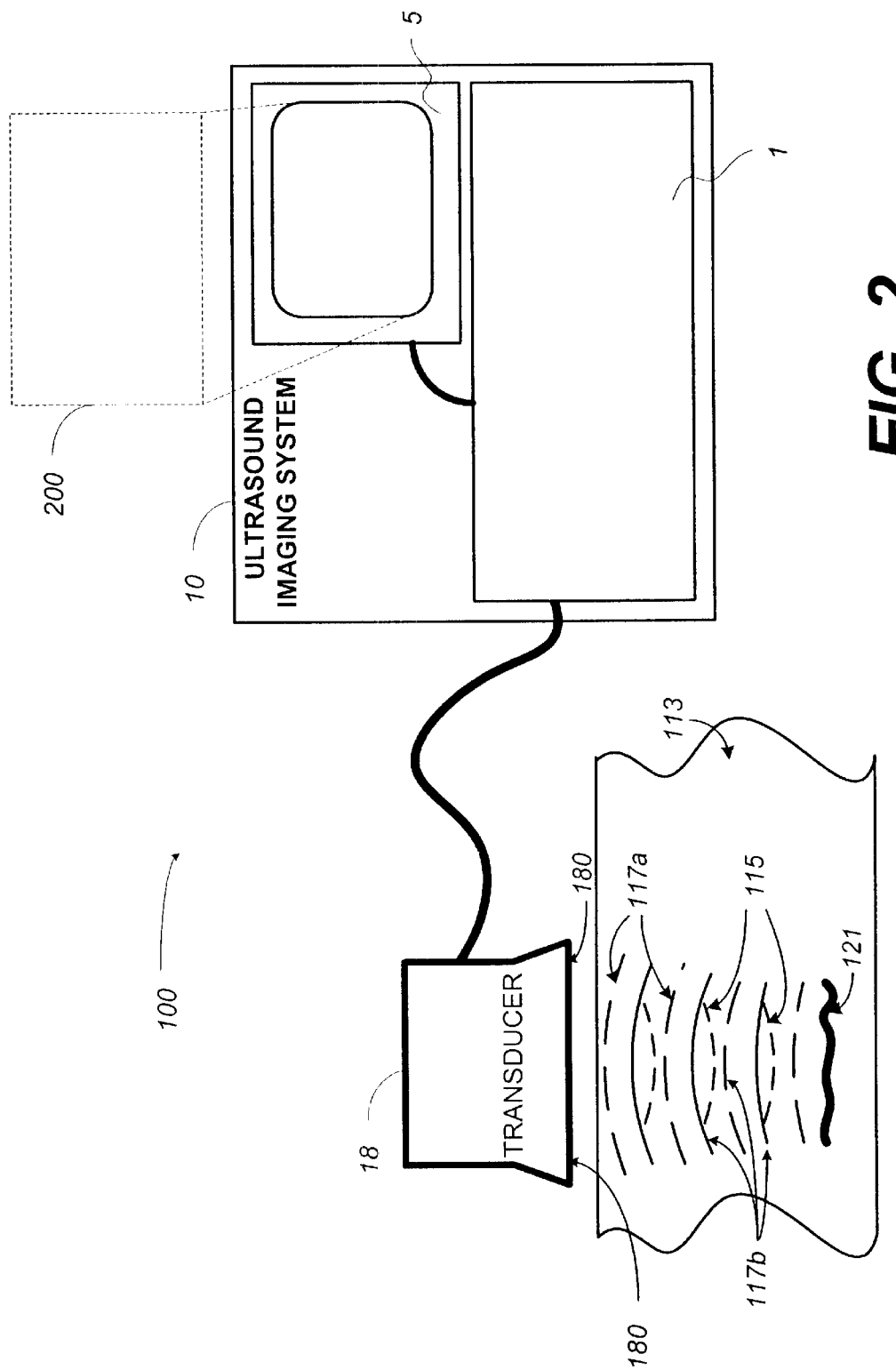
FIG. 2 is a diagram illustrating the use of the ultrasound imaging system of FIG. 1 in a medical diagnostic environment.

Having described the architecture and operation of the ultrasound imaging system 10 of FIG. 1, attention is now directed to FIG. 2, which illustrates the general diagnostic environment where the ultrasound imaging system 10 of FIG. 1 may use the method of the present invention to improve a two-dimensional ultrasound image.

In this regard, the diagnostic environment where the ultrasound imaging system 10 of FIG. 1 may use the method of the present invention is illustrated by way of a diagram in FIG. 2 and is generally denoted by reference numeral 100. As illustrated in FIG. 2, an ultrasound imaging system 10 in accordance with the present invention may be disposed in a diagnostic environment 100 comprising a patient under test 113 and a transducer 18. As illustrated in FIG. 2, the transducer 18 may be placed into position over a portion of the anatomy of a patient under test 113 by a user/operator (not shown) of the ultrasound imaging system 10. As shown in FIG. 2, a plurality of transmit pulses 115 may emanate from the transducer in response to the ultrasound electronics system 1 as described hereinabove. When the transmit pulses (ultrasound energy) 115 encounter a tissue layer of the patient under test 113 that is receptive to ultrasound insonification, the multiple transmit pulses 115 penetrate the tissue layer 113. As long as the magnitude of the multiple ultrasound pulses exceeds the attenuation affects of the tissue layer 113, the multiple ultrasound pulses 115 will reach an internal target 121. Those skilled in the art will appreciate that tissue boundaries or intersections between tissues with different ultrasonic impedances will develop ultrasonic responses at the fundamental transmit frequency of the plurality of ultrasound pulses 115. Tissue insonified with ultrasonic pulses will develop fundamental ultrasonic responses that may be distinguished in time from the transmit pulses in order to convey information from the various tissue boundaries within a patient.

Those ultrasonic reflections of a magnitude that exceed that of the attenuation affects from traversing tissue layer 113 may be monitored and converted into an electrical signal by the combination of the RF switch 16 and the transducer 18 as previously described with regard to FIG. 1. As further illustrated in the diagram of FIG. 2, the ultrasound electronics system 1 and the display electronics system 5 may work together to produce an ultrasound display image 200 derived from the plurality of ultrasonic echoes 117.

Harmonic Image Formation

Those skilled in the art will appreciate that tissue boundaries or intersections between tissues with different ultrasonic impedances will develop ultrasonic responses at both the fundamental frequency as well as at harmonics of the fundamental frequency of the plurality of ultrasound pulses 115. Tissue insonified with ultrasonic pulses will develop both fundamental and harmonic ultrasonic responses that may be distinguished in time from the transmit pulses in order to convey information from the various tissue boundaries within a patient. It will be further appreciated that tissue insonified with ultrasonic pulses develops harmonic responses because the compressional portion of the insonified waveforms travels faster than the rarefactional portions. The different rates of travel of the compressional and the rarefactional portions of the waveforms causes the wave to distort producing a harmonic signal which is reflected or scattered back through the various tissue boundaries.

In a preferred embodiment, the ultrasound imaging system 10 in accordance with the present invention both transmits and receives a plurality of ultrasound pulses at a fundamental frequency. Those skilled in the art will appreciate that harmonic responses may be received by a transducer 18 having an appropriately wide bandwidth to simultaneously transmit at a fundamental frequency and receive associated responses at a harmonic frequency thereof. While fundamental imaging is used in the preferred embodiment, both fundamental and harmonic imaging are contemplated and within the scope of the present invention.

As further illustrated in FIG. 2, fundamental responses and harmonic responses may be depicted by ultrasonic echoes 117a and 117b respectively. It is significant to note that while FIG. 2 illustrates a second harmonic response to the incident multiple ultrasound transmit pulses 115 impinging the internal target 121 other harmonic responses may also observed. As by way of example, it is known that subharmonic, harmonic, and ultraharmonic responses may be created at the tissue boundary between a tissue layer 113 and the internal target 121, when the internal target has been perfused with one or more contrast agents. The internal target 121 alone will produce harmonic responses at integer multiples of the fundamental frequency. Various contrast agents on the other hand, have been shown to produce subharmonic, harmonic, and ultraharmonic responses to incident ultrasonic pulses.

Those ultrasonic reflections of a magnitude that exceed that of the attenuation affects from traversing tissue layer 113 (e.g., fundamental, subharmonic, harmonic, and ultraharmonic responses) may be monitored and converted into an electrical signal by the combination of the RF switch 16 and the transducer 18 as previously described with regard to FIG. 1. As further illustrated in the diagram of FIG. 2, the ultrasound electronics system 1 and the display electronics system 5 may work together to produce an ultrasound display image 200 derived from the plurality of ultrasonic echoes 117.

Elevation Image Compounding

Figure 3:
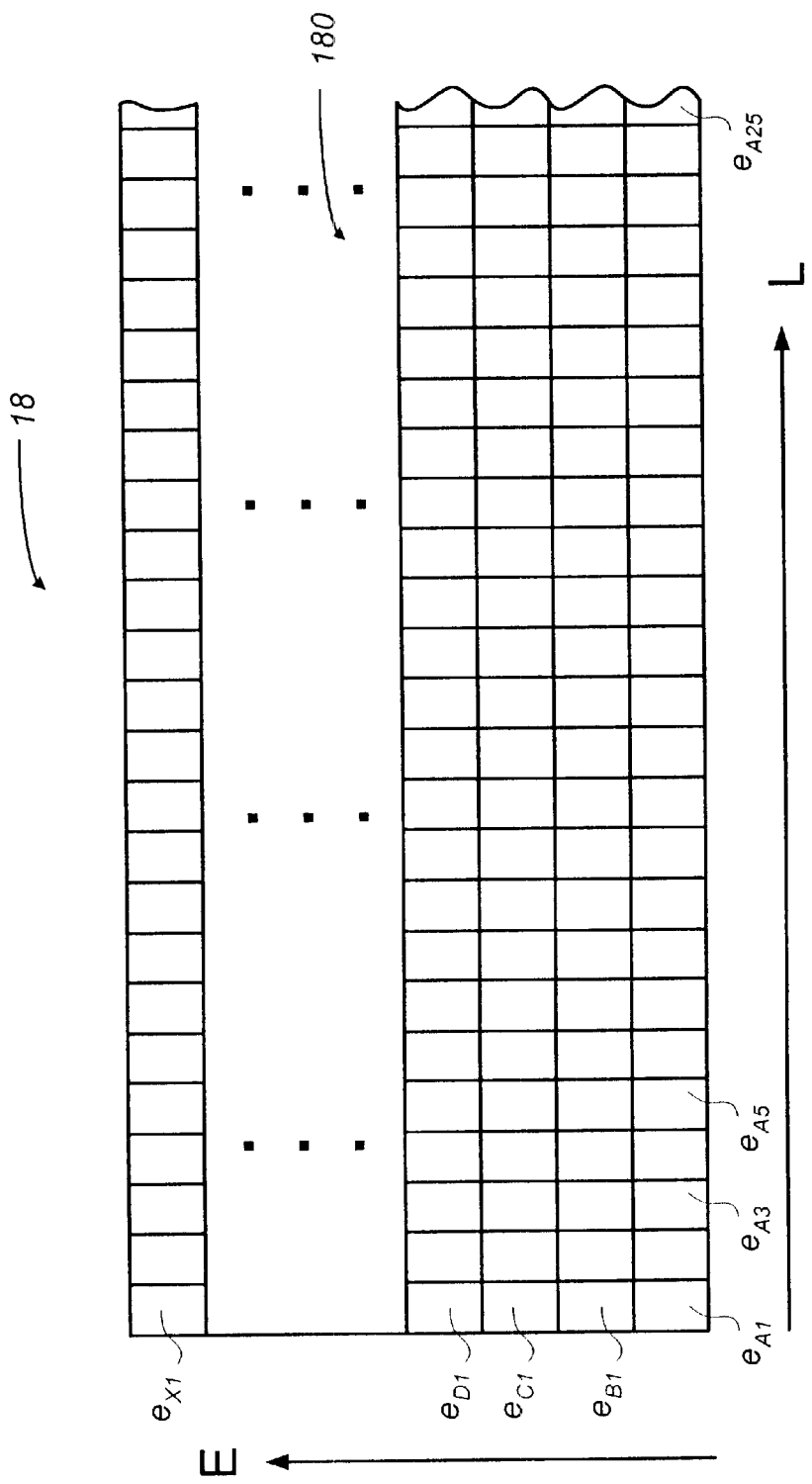
FIG. 3 is a bottom view of an ultrasound transducer element array of a transducer that may be integrated with the ultrasound imaging system of FIGS. 1 and 2.

Having described a diagnostic environment 100 where the ultrasound imaging system 10 of FIG. 1 may use the method of the present invention to produce an improved ultrasound image with regard to the diagram of FIG. 2, reference is now directed to FIG. 3. In this regard, FIG. 3 illustrates a bottom view of a phased array transducer 18 in accordance with the present invention. As illustrated in FIG. 3, the transducer 18 may comprise a plurality of transducer elements generally arranged along a lateral direction, depicted with a horizontal arrow and labeled, "L" as well as a plurality of transducer elements generally arranged along an elevation direction, depicted with a vertical arrow and labeled, "E." As further illustrated in FIG. 3, each of the plurality of transducer elements arranged in the lateral direction are labeled $e_{A1}$, $e_{A2}$, $e_{A3}$, with only a select few of the odd numbered elements actually labeled for simplicity. Similarly, each of the plurality of transducer elements arranged in the elevation direction are herein labeled $e_{A1}$, $e_{B1}$, $e_{C1}$, ..., $e_{X1}$. As is also illustrated in FIG. 3, the plurality of transducer elements may define a transducer array 180. The plane in which the transducer array 180 operates projects outward from the face of the transducer array 180 in a direction perpendicular to a plane formed by the lateral and elevation directions.

In accordance with the principles of the present invention, the transmitted beam emitted in the operating plane can be focused or directed in the lateral direction by actuating transducer elements in a set of grouped transducer elements at slightly different times. Further manipulation in the receive mode serves to steer or focus the ultrasound image plane in a desired lateral direction. Similarly, the transmitted beams can be focused or directed in the elevation direction by actuating transducer elements in a set of grouped transducer elements at slightly different times and further manipulating the transducer elements while in the receive mode to steer and focus the ultrasound image plane in a desired elevation direction.

Having introduced and briefly described a transducer element array 180 as may be implemented on the face of a transducer 18 that may be integrated with the ultrasound imaging system 10 of FIGS. 1 and 2, reference is now directed to FIG. 4. In this regard, FIG. 4 presents a composite of a simplified bottom view and a side view of the transducer 18 illustrating the formation of a laterally steered transmit scan beam. As illustrated in the bottom view of the transducer 18, a transducer array 180 generally arranged rectilinearly with a lateral direction, herein labeled, "L," and an elevation direction, "E," may comprise a transmit aperture 182 formed by a subset of the various transducer elements on the face of the transducer array 180. As shown in the bottom view of FIG. 4, the transmit aperture 182 may comprise a sub-array of transducer elements generally positioned near the center of the transducer array 180. Alternatively, the transmit aperture 182 may comprise a portion of a row of transducer elements arranged substantially in the lateral direction. As is also illustrated in the bottom view of FIG. 4 the transmit aperture 182 may further comprise a transmit apex 162. It is significant to note that the relative position and size of the transmit aperture and the transmit apex introduced in the bottom and side views of FIG. 4, are representative of a non-limiting example only and are not necessarily to scale. It will be appreciated by those skilled in the art, that a stronger set of transmit lines 160 may be provided by a larger transmit aperture.

As illustrated in the side view of the transducer 18, transmitted ultrasound energy may be steered and focused to form a transmit scan beam 170 by applying suitable delays to the excitation signals provided to the various transducer elements within the transmit aperture 182. The transit scan beam 170 is formed by a plurality of transmit lines 160a, 160b, 160c, ..., 160n. Each of the transmit lines 160a, 160b, 160c, ..., 160n may be equally spaced by equal separation angles and may originate from a transmit apex 162. It is significant to note that as previously explained hereinabove the transmit scan beam 170 is formed through the combination of transmitted ultrasound energy and manipulated ultrasound echoes. Those skilled in the art will appreciate that a plurality of transmit lines 160 as illustrated in the side view of FIG. 4 may be formed by controllably receiving the ultrasound echoes from the transducer elements comprising the transmit aperture 182.

Having introduced and briefly described the formation of a laterally steered transmit scan beam 170 with regard to the composite views of FIG. 4, reference is now directed to FIG.

5, which illustrates an alternative method for generating a transmit scan beam 170.

Figure 5:
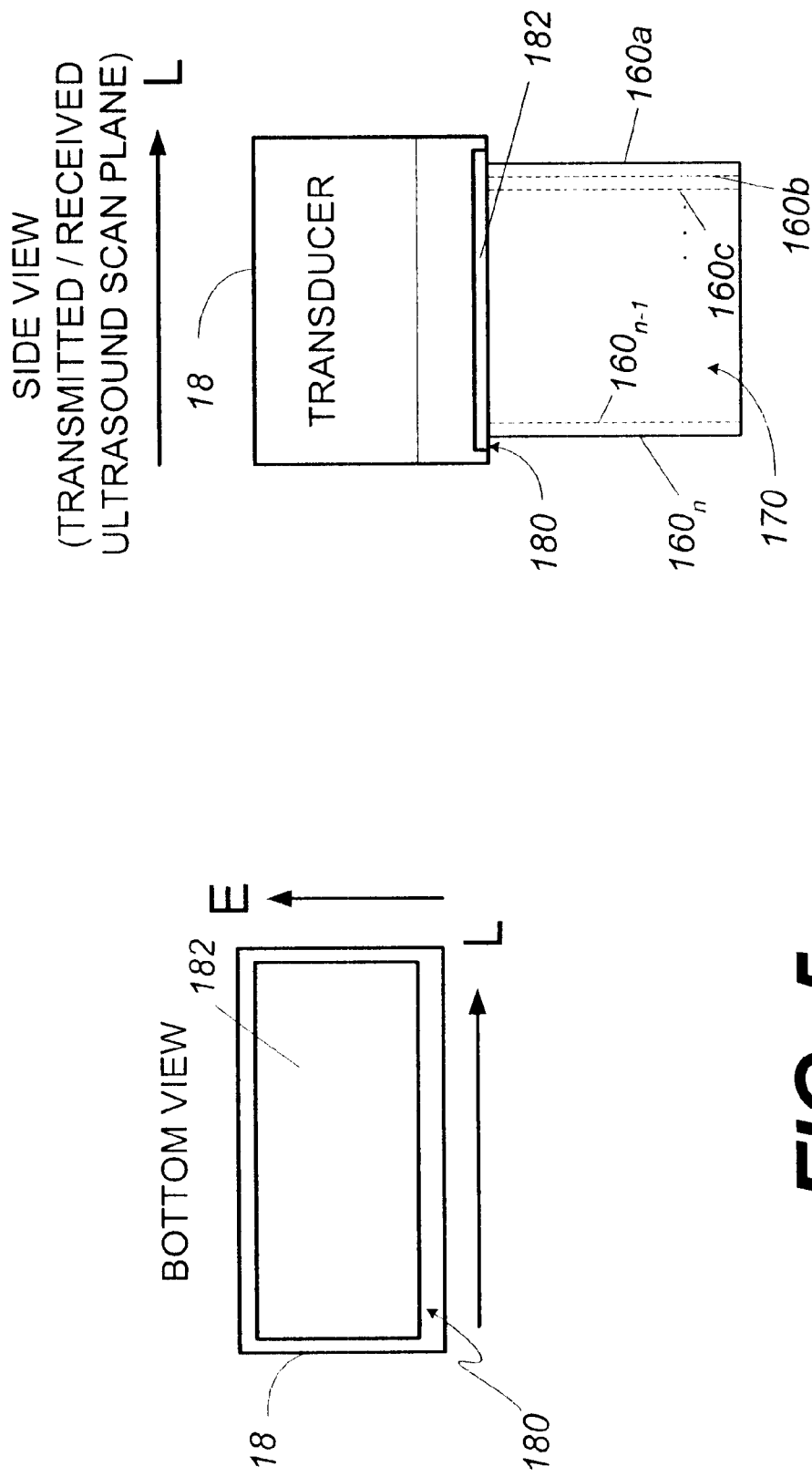
FIG. 5 is a schematic diagram illustrating the generation of another exemplary transmit scan beam that may be formed by the ultrasound imaging system of FIGS. 1 and 2.

As illustrated in the bottom view of FIG. 5, the transducer 18 generally arranged rectilinearly with a lateral direction, herein labeled, "L," and an elevation direction, "E," as in FIG. 4, may comprise a transducer array 180 further defined by a transmit aperture 182 formed by a subset of the various transducer elements on the face of the transducer 18. As also shown in the bottom view of FIG. 5, the transmit aperture 182 may comprise a sub-array of transducer elements generally positioned near the center of the transducer array 180. Alternatively, the transmit aperture 182 may comprise a portion of a row of transducer elements arranged substantially in the lateral direction.

As illustrated in the side view of FIG. 5, transmitted ultrasound energy may be emitted in a substantially perpendicular direction from the face of the transducer array 180 along the transmit aperture 182 such that a plurality of transmit lines 160a, 160b, 160c, . . . , 160n are formed. As further illustrated in the side view of FIG. 5, each of the transmit lines 160a, 160b, 160c, . . . , 160n may be equally spaced by equal separation distances along the various transducer elements forming the transmit aperture 182. As is also shown in the side view of FIG. 5, the plurality of transmit lines 160a, 160b, 160c, . . . , 160n may define a transmit scan beam 170 originating at the face of the transducer array 180. The transmit scan beam 170 may form a plane substantially perpendicular to the lateral and elevation directions of the transducer 18.

It is significant to note that the relative position and size of the transmit aperture 182 revealed in the bottom and side views of FIG. 5, is representative of a non-limiting example only and is not necessarily to scale. Those skilled in the art will appreciate that in order to transmit a more deeply penetrating transmit scan beam, it is preferable to use a substantial portion of the available transducer element array 180 when forming the transmit aperture 182.

Figure 6:
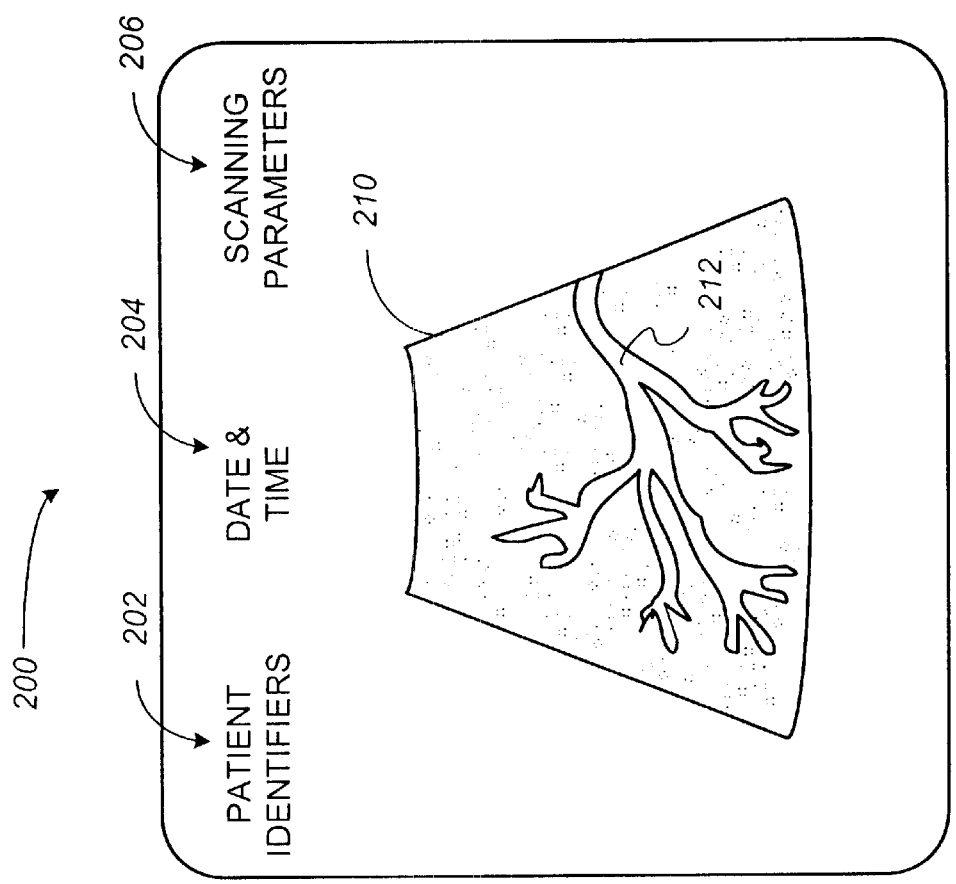
FIG. 6 is a schematic diagram illustrating an exemplary diagnostic image that may be generated by the ultrasound imaging system and observed on the ultrasound imaging display of FIGS. 1 and 2.

Reference is now directed to FIG. 6, which illustrates a diagram depicting image information as it may appear on the ultrasound display image 200 of FIG. 2. In this regard, the ultrasound display image 200 of FIG. 6 may comprise alphanumeric information in the form of patient identifiers 202, date and time identifiers 204 and scanning parameters 206. In addition to the one or more alphanumeric identifiers the ultrasound display image 200 may comprise a real-time ultrasound image 210 of structure in a body such as a portion of the circulatory system 212. A real-time ultrasound image 210 may be used by a clinical technician to ascertain and locate an area of interest. The real-time ultrasound image 210 may be created from tissue generated echoes, ultrasound echoes generated by insonifying one or more contrast agents, or a combination of both tissue generated and contrast agent generated ultrasound echoes. As further illustrated in FIG. 6, the real-time ultrasound image 210 may contain a considerable amount of image speckle. It is significant to note that the diagram of FIG. 6 may represent a snap-shot of a real-time ultrasound display 210 of a portion of the circulatory system 212 of a patient. The ultrasound electronics system 1 may work together with the display electronics 5 of the ultrasound imaging system 10 (see FIG. 1) to create a series of ultrasound images 210 that may be viewed at a suitable frame rate to reveal motion to an observer of the various fluids (e.g., blood in a blood vessel) and tissues within the patient.

The technique for spatial compounding in accordance with the invention may be characterized as simultaneously forming at least two sets of receive or response scan beams for each transmit line. Corresponding receive or response scan beams originating from different vantage points along the face of the transducer 18 may be steered and focused such that they intersect at a predetermined point along the transmit scan beam 170. Multiple points along each transmit beam 170 may be simultaneously targeted to yield first and second sets of receive scan beams which, originate at different spatial vantage points. The received signals corresponding to the two sets of receive scan beams thus represent images of the region of interest from different spatial vantage points obtained simultaneously from ultrasonic responses corresponding to each transmit scan beam 170. It will be appreciated by those skilled in the art that more than two sets of receive scan beams can be formed for each transmit scan beam 170. In accordance with a preferred embodiment of the present invention, the ultrasound imaging system 10 can be configured with suitable electronics as previously described to process the various response signals in parallel. The respective parallel beamformed signals can be detected and combined to provide an image having low speckle artifacts. It will be further appreciated that the spatial compounding technique of the invention can be applied to two or more simultaneous transmit scan beams 170.

The spatial compounding technique described above has several advantages relative to prior art techniques. First, only a single transmit scan beam is required to form two or more uncorrelated receive or response scan beams. In the prior art, transmit scan beams were transmitted from different spatial positions and overlapped in an image plane in the lateral direction. Assuming that only one transmit scan beam can be transmitted at a time, prior art imaging systems required twice the number of transmit scan beams with a corresponding two-to-one reduction in frame rate. An ultrasound imaging system 10 in accordance with the present invention uses parallel processing of the receive information to recover multiple response scan beams without a decrease in frame rate since the response scan beams rely on a shared transmit scan beam.

Second, the spatial compounding technique of the invention produces simultaneous receive or response scan beams. This means that signals from two or more spatially separated vantage points can be combined on the fly without a need for subsequent image buffering and retrieval. Since a combined signal comprising the two or more response signals derived from the two or more response scan beams represents an ultrasound vector along a straight line, scan conversion is simplified relative to prior art spatial compounding techniques. The spatial compounding technique of the present invention permits the scan conversion process to form image signals in the same manner as for a non-compounded image. This is an advantage when scanning with multiple transmit zones, since the zones can be spliced as they normally would without compounding.

Finally, since receive response scan beams are obtained simultaneously, tissue motion within the patient's body does not cause misalignment of the independent images. In the prior art, significant delays could occur between acquisition of the two images, resulting in poor alignment of tissue information.

Figure 7:
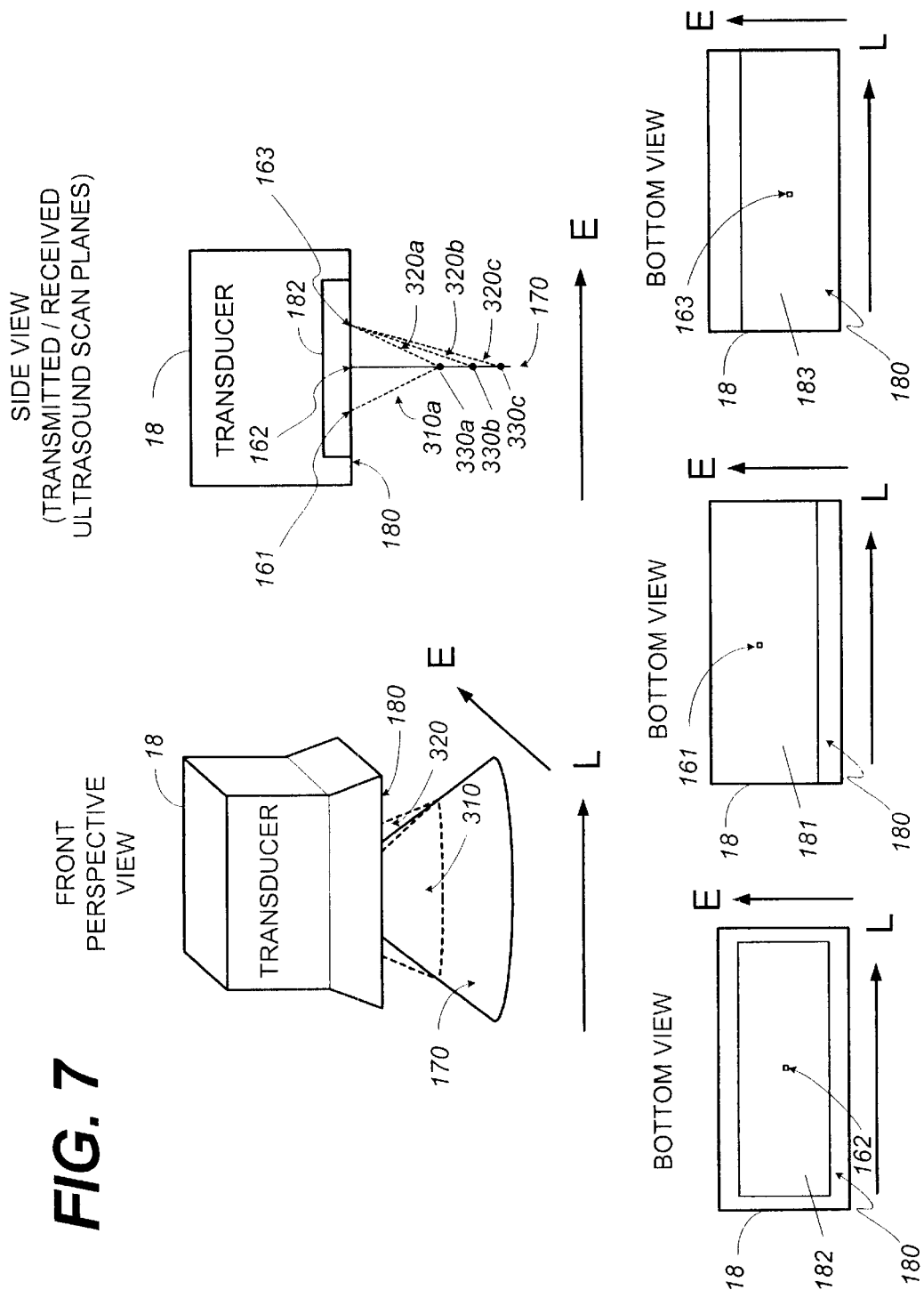
FIG. 7 is a composite of a front perspective, side, and bottom views illustrating the orientation of the plurality of ultrasound image planes in a first embodiment of an ultrasound imaging system of FIGS. 1 and 2.

Reference is now directed to FIG. 7. In this regard, FIG. 7 is a composite of a front perspective, side, and bottom views illustrating the orientation of the plurality of ultrasound scan beams in a first embodiment of an ultrasound imaging system 10 of FIGS. 1 and 2. More specifically, FIG. 7 illustrates the spatial orientation of two ultrasound response scan beams steered in the elevation direction. As illustrated in the various views of FIG. 7, the transducer 18 may comprise an array of transducer elements 180 as previously introduced and described in regard to FIG. 3. As is further illustrated in the front perspective view of FIG. 7, a plurality of transducer elements may be excited with ultrasonic transmit pulses and configured to receive ultrasound echoes from spatially separated vantage points in such a manner to produce a plurality of steered ultrasonic response planes 310, 320. Each of the steered ultrasonic response planes 310, 320 as illustrated may traverse a sector in the lateral direction with the sector expanding with the distance traversed from the face of the array of transducer elements 180. In addition to the steered ultrasonic response planes 310, 320, the transducer elements may be excited with ultrasonic transmit pulses such that a laterally steered transmit scan beam 170 is generated from a portion of the transducer element array 180 that bisects the corresponding originating receive apertures.

The bottom views of FIG. 7 generally illustrate the positioning of various sub-element arrays of the transducer element array 180 of the transducer 18 that may be used to form the various transmit and receive scan planes 170, 310, 320 illustrated and described with regard to the front perspective view of FIG. 7. More specifically, the transducer element array 180 may comprise a transmit aperture 182 responsible for forming the transmit scan plane 170 as described hereinabove with regard to FIGS. 4 and 5. As illustrated in the bottom view of FIG. 7, the transducer element array 180 may further comprise a first receive aperture 181 having a first receive vantage point 161 and a second receive aperture 183 having a second receive vantage point 163. Both the first receive vantage point 161 and the second receive vantage point 163 may be separated in the elevation dimension from the transmit apex 162. It is important to note that the various transmit and receive apertures 182, 181, and 183, respectively as shown in the bottom views of FIG. 7, may substantially overlap one another on the transducer element array 180.

The side view of FIG. 7 further illustrates an exemplary arrangement of the receive vantage points 161, 163 in relation to the transmit apex 162. In accordance with the method for ultrasound imaging of the present invention, the first image vantage point 161 corresponding to the physical location of the sub-element array forming the first receive aperture 181 on the transducer element array 180 may be defined. Similarly, a second image vantage point 163 corresponding to the physical location of the sub-element array forming the second receive aperture 183 on the transducer element array 180 may also be defined.

A technique for receiving multiple ultrasound echoes in response to a transmit scan beam 170 is also illustrated in the side view of FIG. 7. As shown in the side view, multiple ultrasound echoes may be received by the first and second receive apertures 181, 183 of the transducer element array 180 in response to the transmitted ultrasound energy emitted and received from the transmit aperture 182. As is also shown in the side view of FIG. 7 the transmit aperture 182 may define the origination of a transmit scan beam 170. In accordance with the ultrasound imaging method of the present invention, a plurality of received ultrasound echo signals responsive to the transmit scan beam 170 may be processed to form at least two sets of receive scan beams 310, 320 which originate at different spatial vantage points 161, 163. It is significant to note that the receive apertures 181, 183 are not illustrated in the side view of FIG. 7 for simplicity of illustration.

As is also illustrated in the side view of FIG. 7, a first set of receive scan beams 310 (one shown for simplicity of illustration) may be focused and or steered in the elevation dimension such that the set originates at a first spatial vantage point 161 defined by the first receive aperture 181 on transducer element array 180. Similarly, a second set of receive scan beams 320a, 320b, 320c, . . . may be focused and or steered in the elevation dimension such that the second set originates at a second spatial vantage point 163 defined by the second receive aperture 183 on transducer element array 180. The first and second sets of receive scan beams 310, 320 may be steered and focused to intersect at multiple points 330 along the transmit scan beam 170. In particular, receive scan beams 310a and 320a may be simultaneously steered and focused at a point 330a on the transmit scan beam 170. Next, receive scan beams 310b, 320b may be simultaneously steered and focused at a point 330b on the transmit scan beam 170. It will be appreciated that the first and second apertures 181 and 183 may be used to receive a plurality of corresponding receive scan beams 310, 320 at a plurality of points along the transmit scan beam 170.

The received signals corresponding to each pair of first and second receive scan beams 310n, 320n, such as receive scan beams 310b and 320b, simultaneously represent received ultrasound energy from a line formed by the intersection of the receive scan beams 310b and 320b through the transmit scan beam 170. The received signals corresponding to the first and second sets of receive scan beams 310b, 320b represent received ultrasound energy from multiple points along the transmit scan beam 170 represented in the side view by point 330b.

It will be understood that the first and second sets of receive scan beams 310, 320 can be steered and focused both laterally and in elevation such that any number of individual transmit lines used to form the various receive scan beams 310, 320 may be used to obtain image information from any desired number of points along the transmit scan beam 170. It will also be appreciated that a plurality of transmit scan beams 170 may be sequentially generated as one traverses the transducer 18 in the lateral direction. As described hereinabove, the plurality of transmit scan beams 170 may be associated with a plurality of corresponding receive scan beams 310, 320 to derive image information to supply a plurality of image frames.

Since the first and second sets of receive scan beams 310, 320 are obtained from spatially separated vantage points 161, 163 defined by the first and second apertures 181, 183, respectively, they are decorrelated with respect to speckle in the image. The received signals corresponding to the first receive scan beam 310 and the received signals corresponding to the second receive scan beam 320 may be processed and combined as described above to yield a plurality of image signals having reduced speckle in comparison with imaging techniques in which spatial compounding is not utilized.

The processing of received image signals may be repeated for a plurality of transmit scan beams 170 in a scan pattern with appropriate steering and focusing of the receive scan beams 310, 320 at multiple points 330 along each transmit line 160 (FIG. 5). The resulting signals are representative of an image of the region of interest within a corresponding sector traversed by the transmit scan beam 170.

Having described the spatial orientation of a plurality of receive scan beams 170, 310, 320 with regard to a first embodiment of the ultrasound imaging system 10 in the various views of FIG. 7, reference is now directed to FIG. 8, which illustrates multiple variations in the spatial orientation of the various imaging beams. In this regard, FIG. 8 is a composite of a front perspective, side, and bottom views illustrating the orientation of the plurality of ultrasound image beams in a second embodiment of an ultrasound imaging system 10.

More specifically, FIG. 8 illustrates the spatial orientation of two ultrasound response scan beams steered in the elevation direction. As illustrated in the various views of FIG. 8, the transducer 18 may comprise an array of transducer elements 180 as previously introduced and described in regard to FIG. 3. As is further illustrated in the front perspective view of FIG. 8, a plurality of transducer elements may be excited with ultrasonic transmit pulses and configured to receive ultrasound echoes from spatially separated vantage points in such a manner to produce a plurality of steered ultrasonic response planes 310, 320. Each of the steered ultrasonic response planes 310, 320 as illustrated may traverse a sector in the lateral direction with the sector expanding with the distance traversed from the face of the array of transducer elements 180. In addition to the steered ultrasonic response planes 310, 320, the transducer elements may be excited with ultrasonic transmit pulses such that a laterally steered transmit scan beam 170 is generated from a portion of the transducer element array 180 that may be interposed between corresponding originating receive apertures.

The bottom views of FIG. 8 generally illustrate the positioning of various sub-element arrays of the transducer element array 180 of the transducer 18 that may be used to form the various transmit and receive scan planes 170, 310, 320 illustrated and described with regard to the front perspective view of FIG. 8. More specifically, the transducer element array 180 may comprise a transmit aperture 182 responsible for forming the transmit scan plane 170 originating from a transmit apex 162 as described hereinabove with regard to FIGS. 4, 5, and 7. As illustrated in the bottom views of FIG. 8, the transducer element array 180 may comprise a first receive aperture 181 having a first receive vantage point 161 and a second receive aperture 183 having a second receive vantage point 163. Both the first receive vantage point 161 and the second receive vantage point 163 may be separated in the elevation dimension from the transmit apex 162.

The side view of FIG. 8 further illustrates an exemplary arrangement of the receive vantage points 161, 163 in relation to the transmit apex 162. In accordance with the method for ultrasound imaging of the present invention, a first image vantage point 161 corresponding to the physical location of the sub-element array forming the first receive aperture 181 on the transducer element array 180 may be defined. Similarly, a second image vantage point 163 corresponding to the physical location of the sub-element array forming the second receive aperture 183 on the transducer element array 180 may also be defined.

A second exemplary technique for receiving multiple ultrasound echoes in response to a transmit scan beam 170 is illustrated in the side view of FIG. 8. As shown in the side view, multiple ultrasound echoes may be received by the first and second receive apertures 181, 183 of the transducer element array 180 in response to the transmitted ultrasound energy emitted and received from the transmit aperture 182. As is also shown in the side view of FIG. 8, the transmit aperture 182 may define the origination of a transmit scan beam 170. In accordance with this embodiment of the ultrasound imaging method of the present invention, a plurality of received ultrasound echo signals responsive to the transmit scan beam 170 may be processed to form at least two sets of receive scan beams 310, 320 which originate at different spatial vantage points 161, 163, respectively. This embodiment differs from the first embodiment in at least two ways. First, the transmit scan beam 170 is steered in the elevation dimension. Those skilled in the art will appreciate that the additional degree of freedom that results from the capability to steer the transmit scan beam 170 in the elevation direction may be useful in obtaining a two-dimensional image slice at a particularly difficult area within a region of interest.

A second difference between the present embodiment and the first embodiment described above is that each of the receive scan beams 310, 320 may be generated such that the individual scan beams of the individual sets no longer originate from a single (common) vantage point 161, 163 on the transducer element array 180. As illustrated in the side view of FIG. 8, both the first and second set of receive scan beams 320 may be focused and or steered in the elevation dimension such that they originate from unique spatial vantage points 161, 163 defined by the first and second receive apertures 181, 183 on the transducer element array 180 (only the second set of receive scan beams 320a, 320b, 320c, . . . are actually shown for simplicity of illustration). As shown in FIG. 8, the spatially distinct vantage points 161, 163 may be adjusted such that the separation distance between vantage points increases as the depth of the focal point of interest within the tissue under observation increases. As described above, the first and second set of receive scan beams 310, 320 may be focused and or steered in the elevation dimension such that they originate from identifiable and spatially separated vantage points 161 defined by the first receive aperture 181 on transducer element array 180. The first and second sets of receive scan beams 310, 320 may be steered and focused to intersect at multiple points 330 along the transmit scan beam 170. In particular, receive scan beams 310a and 320a may be simultaneously steered and focused to intersect at a line defined by point 330a on the transmit scan beam 170. Next, receive scan beams 310b, 320b may be simultaneously steered and focused to intersect at a line defined by point 330b on the transmit scan beam 170. It will be appreciated that the first and second apertures 181 and 183 may be used to receive a plurality of corresponding receive scan beams 310, 320 at a plurality of points 330 along the transmit scan beam 170.

It will be understood that the first and second sets of receive scan beams 310, 320 cannot only be steered and focused laterally but also in elevation such that any number of individual transmit lines used to form the various receive scan beams 310, 320 may be used to obtain image information from any desired number of points 330 along a transmit scan beam 170 steered in the elevation direction. It will also be appreciated that a plurality of steered transmit scan beams 170 may be sequentially generated as one traverses the transducer 18 in the lateral direction. As described hereinabove, the plurality of transmit scan beams 170 may be associated with a plurality of corresponding receive scan beams 310, 320 to derive image information to supply a plurality of image frames.

Figure 9:
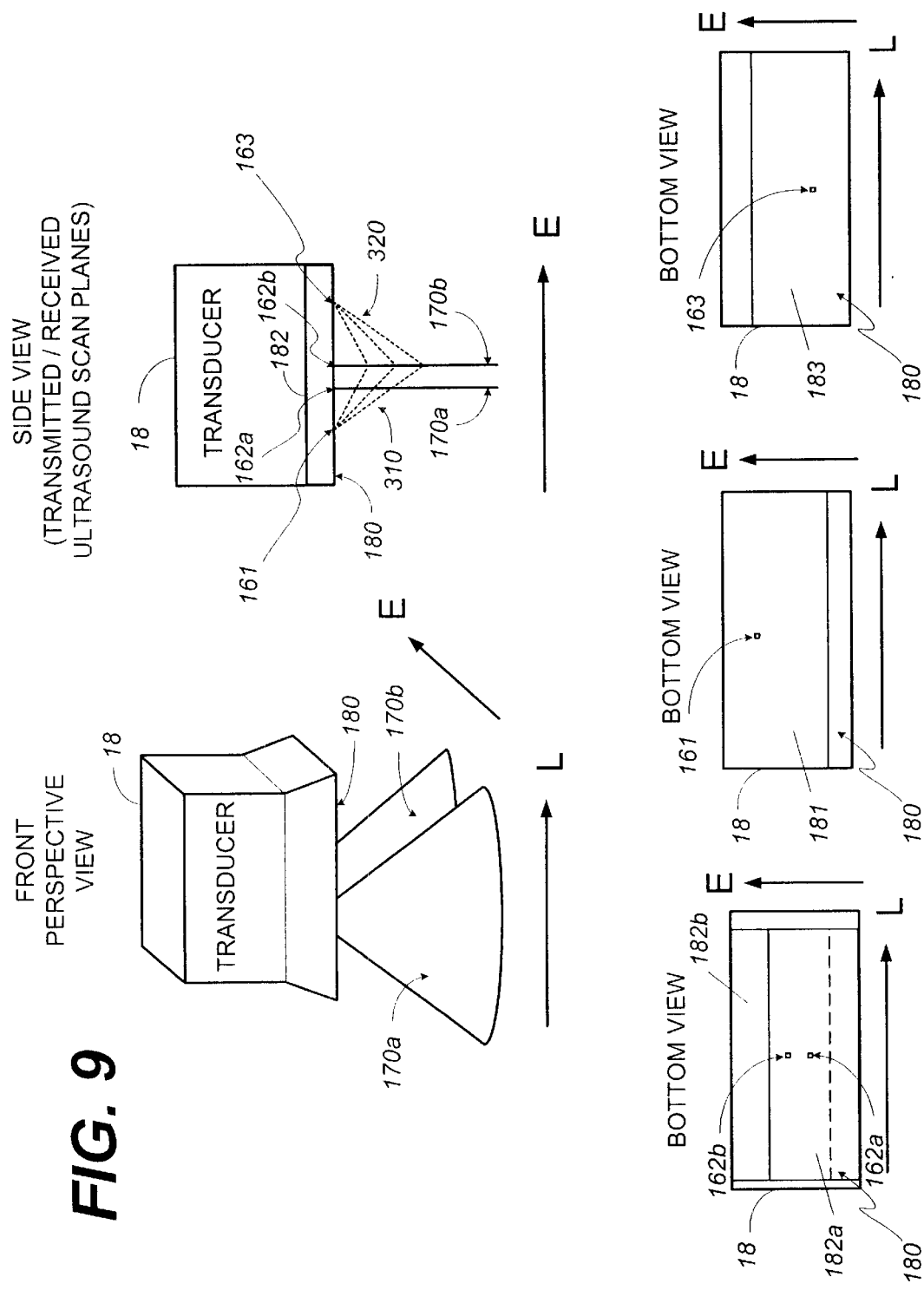
FIG. 9 is a composite of a front perspective, side, and bottom views illustrating the orientation of the plurality of ultrasound image planes in a third embodiment of an ultrasound imaging system of FIGS. 1 and 2.

Having described the spatial orientation of a plurality of receive scan beams with regard to a second embodiment of the ultrasound imaging system 10 in the various views of FIG. 8, reference is now directed to FIG. 9, which illustrates multiple variations in the spatial orientation of the various imaging beams. In this regard, FIG. 9 is a composite of a front perspective, side, and bottom views illustrating the orientation of the plurality of ultrasound image planes in a third embodiment of an ultrasound imaging system 10.

More specifically, FIG. 9 illustrates the use of multiple simultaneously generated transmit scan beams 170a, 170b in cooperation with the spatial orientation of at least two sets of ultrasound response scan beams 310, 320 steered in the elevation direction. As illustrated in the various views of FIG. 9, the transducer 18 may comprise an array of transducer elements 180 as previously introduced and described in regard to FIG. 3. A plurality of transducer elements may be excited with ultrasonic transmit pulses and configured to receive ultrasound echoes from spatially separated vantage points in such a manner to produce a plurality of steered ultrasonic response planes 310, 320. Each of the steered ultrasonic response planes 310, 320 may traverse a sector in the lateral direction with the sector expanding with the distance traversed from the face of the array of transducer elements 180. In addition to the steered ultrasonic response planes 310, 320, the transducer elements may be excited with ultrasonic transmit pulses such that a plurality of transmit scan beams 170a, 170b are generated from closely located sub-portions of the transducer element array 180 that are interposed between the receive apertures 181, 183.

The bottom views of FIG. 9 generally illustrate the positioning of various sub-element arrays of the transducer element array 180 of the transducer 18 that may be used to form the various transmit and receive scan planes 170i a, 170b, 310, 320. More specifically, the transducer element array 180 may comprise at least two transmit apertures 182a, 182b. Each of the transmit apertures 182a, 182b may be responsible for forming a corresponding transmit scan plane 170a, 170b that originates from a corresponding transmit apex 162a, 162b as described hereinabove with regard to FIGS. 4, 5, 7, and 8. As illustrated in the bottom views of FIG. 9, the transducer element array 180 may further comprise a first receive aperture 181 having a first vantage point 161 and a second receive aperture 183 having a second vantage point 163. Both the first receive aperture 181 and the second receive aperture 183 may be separated in the elevation dimension from the transmit apexes 162a, 162b. Furthermore, both the first and second receive apertures 181 and 183 may be dynamically positioned in the elevation dimension such that a transmit scan beam of interest (e.g., transmit scan beam 170b) is interposed between the resulting vantage points 161, 163. An example of dynamically manipulating ultrasonic phased arrays is disclosed in U.S. Pat. No. 5,322,068, to Thiele et al., entitled, "Method and Apparatus For Dynamically Steering Ultrasonic Phased Arrays," the content of which is hereby incorporated in its entirety.

A technique for receiving multiple ultrasound echoes in response to a plurality of transmit scan beams 170a, 170b is illustrated in the side view of FIG. 9. As shown in the side view, multiple ultrasound echoes may be received by the first and second receive apertures 181, 183 of the transducer element array 180 in response to the transmitted ultrasound energy emitted and received from the transmit aperture 182b. As is illustrated in the side view of FIG. 9, the transmit apertures 182b may define the origination of respective transmit scan beams 170b. In a similar manner, a second set of receive apertures (not shown) may be dynamically positioned in the elevation dimension such that a transmit scan beam of interest (e.g., transmit scan beam 170a) is interposed between the resulting vantage points 161, 163. As previously described, the second set of receive apertures may generate a plurality of receive scan beams (not shown) that intersect each other along the transmit scan beam 170b. This embodiment differs from the first two embodiments in that a plurality of simultaneously generated transmit scan beams 170 are used in cooperation with first and second receive apertures 181, 183 respectively to obtain image echoes. Those skilled in the art will appreciate that the additional transmit scan beams 170 may result in a reduction in the scan rate in exchange for the additional image information.

It will be appreciated that the first and second apertures 181 and 183 may be used to receive a plurality of corresponding receive scan beams 310, 320 at a plurality of points along each of the transmit scan beams 170. It will also be understood that the first and second sets of receive scan beams 310, 320 can be steered and focused both laterally and in the elevation direction such that any number of individual transmit lines used to form the various receive scan beams 310, 320 may be used to obtain image information from any desired number of points along a transmit scan beam 170 steered in the elevation direction. It will be further appreciated that a plurality of steered transmit scan beams 170 may be sequentially generated as one traverses the transducer 18 in the lateral direction. As described hereinabove, the plurality of transmit scan beams 170 may be associated with a plurality of corresponding receive scan beams 310, 320 to derive image information to supply a plurality of image frames.

Having described the spatial orientation of a plurality of receive scan beams with regard to a third embodiment of the ultrasound imaging system 10 in the various views of FIG. 9, reference is now directed to FIG. 10, which illustrates multiple variations in the spatial orientation of the various imaging beams. In this regard, FIG. 10 is a composite of a front perspective, side, and bottom views illustrating the orientation of the plurality of ultrasound image planes in a fourth embodiment of an ultrasound imaging system 10.

More specifically, FIG. 10 illustrates the use of multiple simultaneously generated transmit scan beams 170a, 170b in cooperation with the spatial orientation of at least two sets of ultrasound response scan beams 310, 320 steered in the elevation direction. As illustrated in the various views of FIG. 10, the transducer 18 may comprise an array of transducer elements 180 as previously introduced and described in regard to FIG. 3. A plurality of transducer elements may be excited with ultrasonic transmit pulses and configured to receive ultrasound echoes from spatially separated vantage points in such a manner to produce a plurality of steered ultrasonic response planes 310, 320. Each of the steered ultrasonic response planes 310, 320 may traverse a sector in the lateral direction with the sector expanding with the distance traversed from the face of the array of transducer elements 180. In addition to the steered ultrasonic response planes 310, 320, the transducer elements may be excited with ultrasonic transmit pulses such that a plurality of transmit scan beams 170a, 170b are generated from closely located sub-portions of the transducer element array 180 that are interposed between the receive apertures 181, 183, such that the transmit scan beams 170a, 170b appear to originate from a single transmit apex 162.

The bottom views of FIG. 10 generally illustrate the positioning of various sub-element arrays of the transducer element array 180 of the transducer 18 that may be used to form the various transmit and receive scan planes 170a, 170b, 310, 320. More specifically, the transducer element array 180 may comprise a single transmit aperture 182 responsible for generating two transmit scan beams 170a, 170b, controllably manipulated in the elevation direction such that they originate from a single transmit apex 162. In an alternative embodiment, two transmit apertures 182a, 182b may be responsible for forming corresponding transmit scan planes 170*a*, 170*b* that originate from a common transmit apex 162 as described hereinabove with regard to FIGS. 4, 5, 7, 8, and 9. As illustrated in the bottom views of FIG. 9, the transducer element array 180 may further comprise a first receive aperture 181 having a first vantage point 161 and a second receive aperture 183 having a second vantage point 163. Both the first receive aperture 181 and the second receive aperture 183 may be separated in the elevation dimension from the transmit apex 162. Furthermore, both the first and second receive apertures 181 and 183 may be dynamically positioned in the elevation dimension such that a transmit scan beam of interest (e.g., transmit scan beam 170*b*) is interposed between the resulting vantage points 161, 163.

A technique for receiving multiple ultrasound echoes in response to a plurality of transmit scan beams 170*a*, 170*b* is illustrated in the side view of FIG. 10. As shown in the side view, multiple ultrasound echoes may be received by the first and second receive apertures 181, 183 of the transducer element array 180 in response to the transmitted ultrasound energy emitted and received from the transmit aperture 182. As is illustrated in the side view of FIG. 10, the transmit aperture 182 may define the origination of respective transmit scan beams 170*a*, 170*b*. As previously described, a plurality of receive apertures may generate a plurality of receive scan beams 310, 320 that intersect each other along the transmit scan beam 170*b*. This embodiment differs from the third embodiment in that a plurality of simultaneously generated transmit scan beams 170*a*, 170*b* are not substantially parallel.

It will be appreciated that the first and second apertures 181 and 183 may be used to receive a plurality of corresponding receive scan beams 310, 320 at a plurality of points along each of the transmit scan beams 170. It will also be understood that the first and second sets of receive scan beams 310, 320 can be steered and focused both laterally and in the elevation direction such that any number of individual transmit lines used to form the various receive scan beams 310, 320 may be used to obtain image information from any desired number of points along a transmit scan beam 170 steered in the elevation direction. It will be further appreciated that a plurality of steered transmit scan beams 170 may be sequentially generated as one traverses the transducer 18 in the lateral direction. As described hereinabove, the plurality of transmit scan beams 170 may be associated with a plurality of corresponding receive scan beams 310, 320 to derive image information to supply a plurality of image frames.

It is significant to note that the transducer side views of FIGS. 9 and 10 reveal exemplary orientations wherein one of the transmit scan beams 170*b* substantially bisects the sets of receive scan beams 310, 320 having receive vantage points 161, 163, respectively. The system and method for ultrasound imaging may take advantage of a plurality of such arrangements and is not limited to the case where a transmit scan beam 170 is surrounded by substantially equidistant receive vantage points 161, 163.

It is significant to further note that controlled manipulation of the ultrasound image plane in the elevation direction requires a means to steer in the elevation direction. For example, this may be accomplished with an adjustable transducer lens, a motor actuator, or a two-dimensional array of elements, which allow electronic steering in the elevation direction. In the preferred embodiment, a two-dimensional array is used to permit ultrasonic image plane control in the elevation direction. Other systems and methods for beam steering in the elevation direction are contemplated and are in accordance with the teachings of the present invention. For example, an electronically steered transducer array 180 may be scanned via a mechanical means, such as but not limited to, a motor, or a fluid which changes its index of refraction, etc. By way of further example, a mechanically scanned transducer can also be used with the ultrasound imaging system 10. The mechanically scanned transducer may use electronic steering in the elevation plane for image compounding and a motorized apparatus to manipulate the transmit pulses in the lateral or "scan" plane.

As previously described, a plurality of echoes with differing vantage points relative to the elevation aspect of the transducer may be used to spatially compound in the elevation direction. Furthermore, images spatially compounded in the elevation direction may be further mathematically combined with images spatially compounded in the lateral direction to obtain an image of a desired target object 121 (see FIG. 2). This two-dimensional spatial compounding may further reduce undesired image speckle by averaging out the subsequent speckle variations between the plurality of images.

It is significant to note that the two-dimensional phased array transducer 18 of FIG. 3 is presented by way of example only to illustrate the concepts of the present invention. The labels illustrated therein were not selected to convey a limitation as to the size of the two-dimensional array of transducer elements in either the lateral or the elevation directions. It is also significant to note that the various receive apertures 181, 183 illustrated hereinabove with regards to FIGS. 7–10 may be adjusted laterally such that electronically manipulated vantage points may be concurrently separated in both the elevation and the lateral dimensions to enable two-dimensional spatial compounding. Furthermore, as referenced hereinabove, spatial compounding in the elevation direction may be performed using an adjustable transducer lens, a motor actuator, mechanical guides, and the like, that are capable of communicating the relative position of the transmitting transducer elements within the transducer 18.

Figure 11:
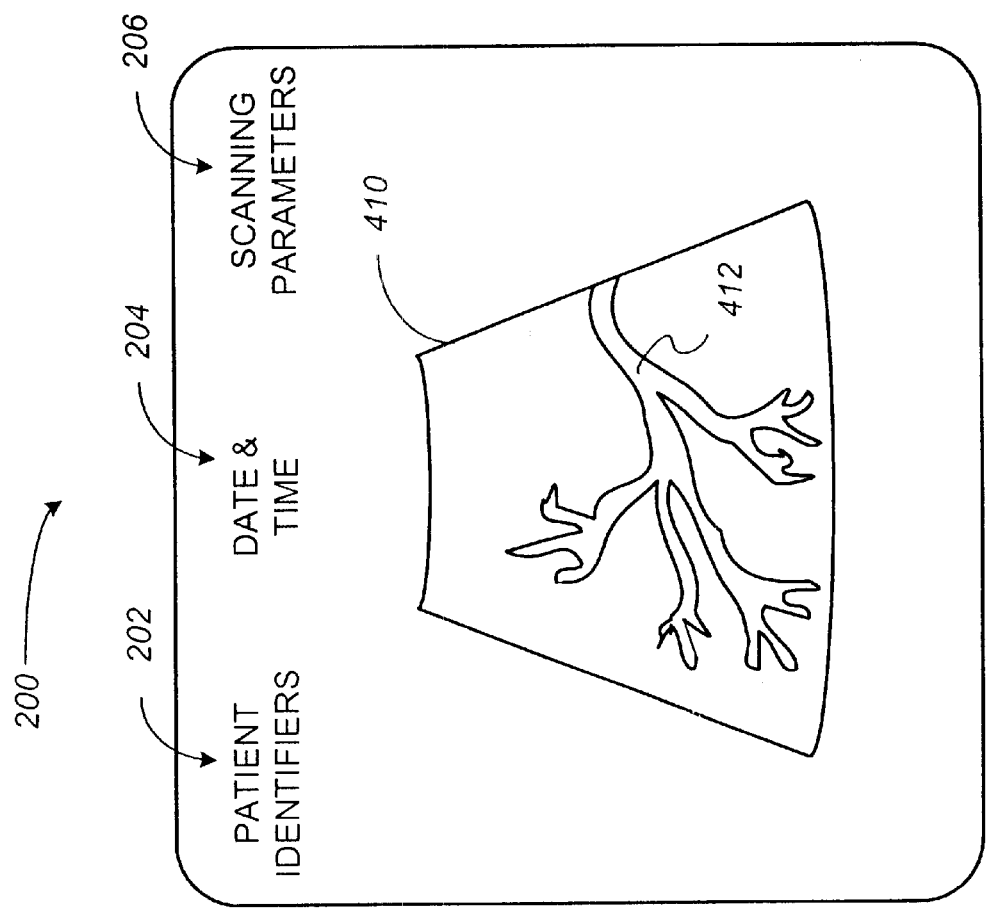
FIG. 11 is a schematic diagram illustrating a diagnostic image that may be generated by the ultrasound imaging system and observed on the ultrasound imaging display of FIGS. 1 and 2.

Having described several alternative orientations for a plurality of ultrasound scan beams with regard to FIGS. 7 through 10, reference is now directed to FIG. 11, which illustrates a diagram depicting image information as it may appear on the ultrasound display image 200 of FIG. 2 after spatial compounding in both the elevation and lateral directions. In this regard, the ultrasound display image 200 of FIG. 11 may comprise alphanumeric information in the form of patient identifiers 202, date and time identifiers 204 and scanning parameters 206. In addition to the one or more alphanumeric identifiers the ultrasound display image 200 may comprise a real-time ultrasound image 410 of structure in a body such as a portion of the circulatory system 412. The real-time ultrasound image 410 maybe created from tissue generated echoes, ultrasound echoes generated by insonifying one or more contrast agents, or a combination of both tissue generated and contrast agent generated ultrasound echoes wherein the transmit pulses have differing directions in both the lateral and elevation directions. As further illustrated in FIG. 11, the real-time ultrasound image 410 may reveal a substantial reduction in image speckle when compared with the image of FIG. 6. It is significant to note that the diagram of FIG. 11 may represent a snap-shot of a real-time ultrasound display 410 of a portion of the circulatory system 412 of a patient. The ultrasound electronics system 1 may work together with the display electronics system 5 of the ultrasound imaging system 10 (see FIG. 1) to create a series of ultrasound images 410 that may be viewed at a suitable frame rate to reveal motion to an observer of the various fluids (e.g., blood in a blood vessel) and tissues within the patient.

It is significant to note that software required to perform the functional activities illustrated in FIG. 1 and or the mathematical combinations and data manipulations necessary to spatial compound ultrasound images in two-dimensions may comprise an ordered listing of executable instructions for implementing logical functions. As such, the software can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

It should be emphasized that the above-described embodiments of the present invention, particularly, any "preferred" embodiment(s), are merely possible examples of implementations that are merely set forth for a clear understanding of the principles of the invention. Furthermore, many variations and modifications may be made to the above-described embodiments of the invention without departing substantially from the spirit and principles of the invention. All such modifications and variations are intended to be taught by the present disclosure, included within the scope of the present invention, and protected by the following claims.

Therefore, having thus described the invention, at least the following is claimed:

1. An ultrasound imaging system, comprising:
   a transmitter configured to generate a plurality of time interleaved transmit signals;
   a transducer in communication with the transmitter, said transducer having a lateral direction and an elevation direction, said transducer configured to translate and receive a plurality of time interleaved signals such that a plurality of controllably steered transmit lines in the lateral direction form a transmit scan beam, said transducer further configured to receive a plurality of ultrasonic responses reflected by the various tissues in a volume under observation insonified by the transmit scan beam at a plurality of vantage points separated in elevation, said transducer further configured to convert the received ultrasonic responses into a plurality of associated receive signals;
   a receiver in communication with the transducer configured to receive the plurality of receive signals, wherein the receiver is configured to acquire a plurality of response scan beams using a beamforming technique;
   a signal processor in communication with the receiver configured to mathematically combine image information derived from the plurality of response scan beams into a display signal; and
   a monitor in communication with the signal processor configured to convert the display signal into an image.

2. The system of claim 1, wherein the transducer comprises at least a first receive aperture and a second receive aperture configured to generate a plurality of ultrasound response scan line sets such that a first response scan line set originates from a first vantage point and a second response scan line set originates from a second vantage point, respectively.

3. The system of claim 2, wherein the plurality of ultrasound response scan lines form a plurality of dynamically manipulated ultrasound response scan beams that originate from at least the first vantage point and the second vantage point, respectively.

4. The system of claim 3, wherein the plurality of ultrasound response scan beams that originate from the first vantage point form a first set of response scan beams and the plurality of ultrasound response scan beams that originate from the second vantage point form a second set of response scan beams.

5. The system of claim 4, wherein the first and second set of response scan beams are controllably manipulated such that corresponding individual response scan beams from both the first and second set of response scan beams intersect each other at the transmit scan beam.

6. The system of claim 5, wherein the transducer is a phased-array transducer.

7. The system of claim 5, wherein the transducer is a linear-array transducer.

8. The system of claim 5, wherein the transducer is a curved linear-array transducer.

9. The system of claim 5, wherein the signal processor is configured to average the image information contained within the plurality of response signals to spatially compound in the elevation direction.

10. The system of claim 5, wherein the transmit scan beam is controllably steered in the elevation direction and the plurality of ultrasound response scan beams steered in elevation originate from a plurality of corresponding vantage points such that a separation distance between subsequent vantage points increases with the depth of the focal point of interest along the transmit scan beam.

11. The system of claim 8, wherein the curved linear-array forms a surface comprising a plurality of transducer elements that are substantially curvilinear in the elevation direction.

12. The system of claim 9, wherein the transmit scan beam is controllably steered in the elevation direction.

13. The system of claim 9, wherein the transducer is configured to translate a plurality of time interleaved transmit signals into a plurality of associated ultrasonic pulses controllably adjustable in the lateral direction, and wherein the signal processor is further configured to spatially compound the plurality of image planes in the lateral direction.

14. The system of claim 11, wherein the transducer in combination with the transmitter and receiver is further configured to transmit a plurality of transmit signals that vary in frequency, and wherein the signal processor is further configured to frequency compound a plurality of image planes generated in response to the plurality of frequency varied transmit signals.

15. The system of claim 1, wherein the transducer is configured with electronics configured to apply a plurality of scan sequences responsive to control signals originating within the transmitter and the receiver.

16. The system of claim 15, wherein the transducer is configured with electronics configured to select an angle and focal point to manipulate a transmitted pulse of ultrasound energy in a desired direction.

17. The system of claim 15, wherein the transducer is configured with electronics configured to dynamically vary a receive steering angle and focal point to manipulate received ultrasound energy along at least one virtual scan line in a desired direction.

18. The system of claim 16, wherein the transducer in combination with the transmitter and receiver is configured to generate at least two substantially parallel transmit scan beams separated in the elevation dimension.

19. The system of claim 16, wherein the transducer is configured with a plurality of dynamically focused receive apertures defining a plurality of respective vantage points.

20. The system of claim 16, wherein the transducer in combination with the transmitter and receiver is configured to generate at least two transmit scan beams that share a common origination apex and propagate from the transducer such that a controllable angle is formed therebetween.

21. A method for reducing speckle in an ultrasound image, comprising the following steps:

generating a transmit scan beam substantially perpendicular to the face of a transducer element array such that the transmit scan beam originates from a transmit aperture formed by a first sub-portion of the transducer element array;

generating a first set of ultrasound response scan beams originating from a first vantage point defined by a first receive aperture formed by a second sub-portion of the transducer element array that is displaced in elevation from the transmit aperture;

generating a second set of ultrasound response scan beams originating from a second vantage point defined by a second receive aperture formed by a third sub-portion of the transducer element array;

controllably steering corresponding pairs of ultrasound response beams from the first and second sets such that the corresponding response beams converge at the transmit beam;

recovering image information from the first and second set of ultrasound response scan beams from objects insonified with the transmit scan beam; and compounding the image information in the elevation direction.

22. The method of claim 21, wherein the step of generating a transmit scan beam is replaced with generating a plurality of transmit scan beams having a common direction and separated in elevation into a volume of interest.

23. The method of claim 21, wherein the step of recovering is performed with a beamforming technique.

24. The method of claim 21, wherein the step of compounding is performed in conjunction with image compounding in the lateral direction.

25. The method of claim 21, wherein the step of compounding is performed in conjunction with frequency compounding.

26. An ultrasound imaging system, comprising:
means for generating a transmit scan beam;
means for generating a plurality of ultrasound response scan beams steered in elevation such that the response scan beams originate from at least two vantage points such that the response beams intersect at the transmit scan beam;
means for recovering image information derived from the plurality of ultrasound image planes;
means for spatially compounding the recovered image information in the elevation dimension; and
means for converting the spatially compounded image information such that it may be viewed by an operator.

27. The system of claim 26, wherein the means for generating a plurality of ultrasound response scan beams generates ultrasound response beams that are separated in the elevation dimension.

28. The system of claim 26, wherein the means for recovering image information from the plurality of ultrasound response scan beams comprises a parallel beamforming technique.

29. The system of claim 26, wherein the means for generating a plurality of ultrasound response scan beams is accomplished with a one-dimensional mechanically scanned transducer array.

30. The system of claim 26, wherein the means for generating a plurality of ultrasound response scan beams is accomplished with an electronically manipulated two-dimensional array.

31. The system of claim 26, wherein the means for spatially compounding is further configured to perform elevation compounding in conjunction with at least one other method for compounding an image selected from the group consisting of lateral compounding and frequency compounding.

32. An ultrasound imaging system, comprising:
a transmitter configured to generate a plurality of time interleaved transmit signals;
a transducer in communication with the transmitter, said transducer having a lateral direction and an elevation direction, said transducer configured to translate and receive a plurality of time interleaved signals such that a plurality of controllably steered transmit lines in the lateral direction form a transmit scan beam, said transducer further configured to receive a plurality of ultrasonic responses reflected by tissues insonified by the transmit scan beam at a plurality of vantage points separated in elevation, said transducer further configured to convert the received ultrasonic responses into a plurality of associated receive signals;
said transducer comprises at least a first receive aperture and a second receive aperture configured to generate a plurality of ultrasound response scan line sets such that a first response scan line set originates from a first vantage point and a second response scan line set originates from a second vantage point; said plurality of ultrasound response scan lines form a plurality of dynamically manipulated ultrasound response scan beams;
a receiver in communication with the transducer configured to receive the plurality of receive signals, wherein the receiver is configured to acquire the plurality of response scan beams using a beamforming technique;
a signal processor in communication with the receiver configured to mathematically combine image information derived from the plurality of response scan beams into a display signal; and
a monitor in communication with the signal processor configured to convert the display signal into an image.

* * * * *